(12) United States Patent
Belson et al.

(10) Patent No.: US 11,925,778 B2
(45) Date of Patent: *Mar. 12, 2024

(54) INTRAVENOUS CATHETER INSERTION DEVICE

(71) Applicant: Vascular Pathways, Inc., Salt Lake City, UT (US)

(72) Inventors: Amir Belson, Los Altos, CA (US); Gregory W. Hall, Los Gatos, CA (US); Scott A. Daniel, Hayward, CA (US); Robert Brommer, Fremont, CA (US)

(73) Assignee: Vascular Pathways, Inc., Salt Lake City, UT (US)

( * ) Notice: Subject to any disclaimer, the term of this patent is extended or adjusted under 35 U.S.C. 154(b) by 372 days.

This patent is subject to a terminal disclaimer.

(21) Appl. No.: 16/867,349

(22) Filed: May 5, 2020

(65) Prior Publication Data
US 2020/0261703 A1    Aug. 20, 2020

Related U.S. Application Data

(63) Continuation of application No. 16/292,076, filed on Mar. 4, 2019, now Pat. No. 11,020,571, which is a
(Continued)

(51) Int. Cl.
*A61M 25/09*       (2006.01)
*A61M 5/32*        (2006.01)
(Continued)

(52) U.S. Cl.
CPC .. *A61M 25/09041* (2013.01); *A61M 25/0606* (2013.01); *A61M 25/0631* (2013.01);
(Continued)

(58) Field of Classification Search
CPC ........ A61M 25/09041; A61M 25/0606; A61M 25/0631; A61M 25/09; A61M 5/3232;
(Continued)

(56) References Cited

U.S. PATENT DOCUMENTS 2,211,975 A    8/1940   Hendrickson
2,259,488 A    10/1941  Raiche
(Continued)

FOREIGN PATENT DOCUMENTS

AU    691141 B2    5/1998
AU    710967 B2    9/1999
(Continued)

OTHER PUBLICATIONS

U.S. Appl. No. 14/099,050, filed Dec. 6, 2013 Advisory Action dated Jun. 1, 2017.
(Continued)

*Primary Examiner* — Lauren P Farrar
(74) *Attorney, Agent, or Firm* — Rutan & Tucker LLP

(57) ABSTRACT

A method for treating a patient using a catheter insertion device. The catheter insertion device includes a housing, a needle, a catheter, a guidewire, and a thumbwheel. The needle extends through the catheter such that a distal end of the needle extends distal of a distal end of the catheter. The guidewire is coupled to the thumbwheel such that rotation of the thumbwheel advances a distal end of the guidewire through a lumen of the needle. The method includes holding the catheter insertion device, inserting the distal end of the needle and catheter into a blood vessel, rotating the thumbwheel to advance the distal end of the guidewire out of the lumen of the needle into the blood vessel, moving the catheter over the guidewire in the blood vessel, and removing the needle and the guidewire from the catheter.

15 Claims, 9 Drawing Sheets

Related U.S. Application Data continuation of application No. 14/866,441, filed on Sep. 25, 2015, now Pat. No. 10,220,191, which is a continuation of application No. 11/577,491, filed as application No. PCT/US2006/026671 on Jul. 6, 2006, now Pat. No. 9,162,037.

(60) Provisional application No. 60/697,333, filed on Jul. 6, 2005.

(51) Int. Cl.
  *A61M 25/01* (2006.01)
  *A61M 25/06* (2006.01)

(52) U.S. Cl.
  CPC ........... *A61M 25/09* (2013.01); *A61M 5/3232* (2013.01); *A61M 5/3234* (2013.01); *A61M 5/3243* (2013.01); *A61M 5/3257* (2013.01); *A61M 25/01* (2013.01); *A61M 25/065* (2013.01); *A61M 2025/09133* (2013.01)

(58) Field of Classification Search
  CPC .. A61M 5/3234; A61M 5/3257; A61M 25/01; A61M 25/065; A61M 2025/09133
  See application file for complete search history.

(56) References Cited

U.S. PATENT DOCUMENTS

| | | |
|---|---|---|
| 2,330,400 A | 9/1943 | Winder |
| D138,589 S | 8/1944 | Brandenburg |
| 3,185,151 A | 5/1965 | Czorny |
| 3,297,030 A | 1/1967 | Czorny et al. |
| 3,416,567 A | 12/1968 | von Dardel et al. |
| 3,469,579 A | 9/1969 | Hubert |
| 3,500,828 A | 3/1970 | Podhora |
| 3,552,384 A | 1/1971 | Pierie et al. |
| 3,572,334 A | 3/1971 | Petterson |
| 3,585,996 A | 6/1971 | Reynolds et al. |
| 3,589,361 A | 6/1971 | Loper et al. |
| 3,592,192 A | 7/1971 | Harautuneian |
| 3,595,230 A | 7/1971 | Suyeoka et al. |
| 3,610,240 A | 10/1971 | Harautuneian |
| 3,682,173 A | 8/1972 | Center |
| 3,766,916 A | 10/1973 | Moorehead et al. |
| 3,884,242 A | 5/1975 | Bazell et al. |
| 3,921,631 A | 11/1975 | Thompson |
| 3,995,628 A | 12/1976 | Gula et al. |
| 4,027,668 A | 6/1977 | Dunn |
| 4,037,600 A | 7/1977 | Poncy et al. |
| 4,079,738 A | 3/1978 | Dunn et al. |
| 4,106,506 A | 8/1978 | Koehn et al. |
| 4,177,809 A | 12/1979 | Moorehead |
| 4,292,970 A | 10/1981 | Hession, Jr. |
| 4,317,445 A | 3/1982 | Robinson |
| 4,345,602 A | 8/1982 | Yoshimura et al. |
| 4,354,491 A | 10/1982 | Marbry |
| 4,368,730 A | 1/1983 | Sharrock |
| 4,387,879 A | 6/1983 | Tauschinski |
| 4,417,886 A | 11/1983 | Frankhouser et al. |
| 4,449,693 A | 5/1984 | Gereg |
| 4,456,017 A | 6/1984 | Miles |
| 4,464,171 A | 8/1984 | Garwin |
| 4,509,534 A | 4/1985 | Tassin, Jr. |
| 4,509,945 A | 4/1985 | Kramann et al. |
| 4,511,359 A | 4/1985 | Vaillancourt |
| 4,512,766 A | 4/1985 | Vailancourt |
| 4,525,157 A | 6/1985 | Vaillancourt |
| 4,581,019 A | 4/1986 | Curelaru et al. |
| 4,585,440 A | 4/1986 | Tchervenkov et al. |
| D287,877 S | 1/1987 | Holewinski et al. |
| 4,728,322 A | 3/1988 | Walker et al. |
| 4,738,659 A | 4/1988 | Sleiman |
| 4,747,831 A | 5/1988 | Kulli |
| 4,767,407 A | 8/1988 | Foran |
| 4,767,408 A | 8/1988 | McFarlane |
| 4,772,264 A | 9/1988 | Cragg |
| 4,772,267 A | 9/1988 | Brown |
| 4,781,703 A | 11/1988 | Walker et al. |
| 4,792,531 A | 12/1988 | Kakihana |
| 4,798,193 A | 1/1989 | Giesy et al. |
| 4,813,934 A | 3/1989 | Engelson et al. |
| 4,826,070 A | 5/1989 | Kakihana |
| 4,828,547 A | 5/1989 | Sahi et al. |
| 4,834,708 A | 5/1989 | Pillari |
| 4,834,718 A | 5/1989 | McDonald |
| 4,840,613 A | 6/1989 | Balbierz |
| 4,840,622 A | 6/1989 | Hardy |
| 4,842,591 A | 6/1989 | Luther |
| 4,846,812 A | 7/1989 | Walker et al. |
| 4,850,961 A | 7/1989 | Wanderer et al. |
| 4,860,757 A | 8/1989 | Lynch et al. |
| 4,869,259 A | 9/1989 | Elkins |
| D304,079 S | 10/1989 | McFarlane |
| 4,871,358 A | 10/1989 | Gold |
| 4,874,377 A | 10/1989 | Newgard et al. |
| 4,883,461 A | 11/1989 | Sawyer |
| 4,883,699 A | 11/1989 | Aniuk et al. |
| 4,894,052 A | 1/1990 | Crawford |
| 4,895,346 A | 1/1990 | Steigerwald |
| 4,900,307 A | 2/1990 | Kulli |
| 4,906,956 A | 3/1990 | Kakihana |
| 4,908,021 A | 3/1990 | McFarlane |
| 4,909,793 A | 3/1990 | Vining et al. |
| 4,911,691 A | 3/1990 | Aniuk et al. |
| 4,913,704 A | 4/1990 | Kurimoto |
| 4,917,102 A | 4/1990 | Miller et al. |
| 4,917,668 A | 4/1990 | Haindl |
| 4,917,671 A | 4/1990 | Chang |
| 4,929,235 A | 5/1990 | Merry et al. |
| 4,935,010 A | 6/1990 | Cox et al. |
| 4,944,725 A | 7/1990 | McDonald |
| 4,944,728 A | 7/1990 | Carrell et al. |
| 4,955,863 A | 9/1990 | Walker et al. |
| 4,961,729 A | 10/1990 | Vaillancourt |
| 4,966,586 A | 10/1990 | Vaillancourt |
| 4,966,589 A | 10/1990 | Kaufman |
| 4,994,042 A | 2/1991 | Vadher |
| 4,994,047 A | 2/1991 | Walker et al. |
| 4,995,866 A | 2/1991 | Amplatz et al. |
| 5,007,901 A | 4/1991 | Shields |
| 5,009,642 A | 4/1991 | Sahi |
| 5,019,048 A | 5/1991 | Margolin |
| 5,019,049 A | 5/1991 | Haining |
| D318,733 S | 7/1991 | Wyzgala |
| 5,034,347 A | 7/1991 | Kakihana |
| 5,047,013 A | 9/1991 | Rossdeutscher |
| D321,250 S | 10/1991 | Jepson et al. |
| 5,053,014 A | 10/1991 | Van Heugten |
| 5,054,501 A * | 10/1991 | Chuttani ............... A61M 25/09 604/528 |
| 5,061,254 A | 10/1991 | Karakelle et al. |
| 5,064,416 A | 11/1991 | Newgard et al. |
| 5,078,694 A | 1/1992 | Wallace |
| 5,078,696 A | 1/1992 | Nedbaluk |
| 5,078,702 A | 1/1992 | Pomeranz |
| 5,084,023 A | 1/1992 | Lemieux |
| 5,085,645 A | 2/1992 | Purdy et al. |
| 5,088,984 A | 2/1992 | Fields |
| 5,093,692 A | 3/1992 | Su et al. |
| 5,098,392 A | 3/1992 | Fleischhacker et al. |
| 5,098,395 A | 3/1992 | Fields |
| 5,098,396 A | 3/1992 | Taylor et al. |
| 5,098,405 A | 3/1992 | Peterson et al. |
| 5,108,375 A | 4/1992 | Harrison et al. |
| 5,108,376 A | 4/1992 | Bonaldo |
| 5,112,312 A | 5/1992 | Luther |
| 5,116,323 A | 5/1992 | Kreuzer et al. |
| 5,120,317 A | 6/1992 | Luther |
| 5,125,906 A | 6/1992 | Fleck |
| 5,135,487 A | 8/1992 | Morrill et al. |
| 5,137,515 A | 8/1992 | Hogan |
| 5,149,326 A | 9/1992 | Woodgrift et al. |
| 5,154,703 A | 10/1992 | Bonaldo |

(56) References Cited

U.S. PATENT DOCUMENTS

| | | |
|---|---|---|
| 5,156,590 A | 10/1992 | Vilmar |
| 5,156,596 A | 10/1992 | Balbierz et al. |
| 5,158,544 A | 10/1992 | Weinstein |
| 5,167,637 A | 12/1992 | Okada et al. |
| 5,176,650 A | 1/1993 | Haining |
| 5,186,168 A | 2/1993 | Spofford et al. |
| 5,186,712 A | 2/1993 | Kelso et al. |
| 5,188,607 A | 2/1993 | Wu |
| 5,190,528 A | 3/1993 | Fonger et al. |
| 5,192,301 A | 3/1993 | Kamiya et al. |
| 5,195,974 A | 3/1993 | Hardy |
| 5,195,980 A | 3/1993 | Catlin |
| 5,195,985 A | 3/1993 | Hall |
| 5,205,830 A | 4/1993 | Dassa et al. |
| 5,215,527 A | 6/1993 | Beck et al. |
| 5,215,528 A | 6/1993 | Purdy et al. |
| 5,217,435 A | 6/1993 | Kring |
| 5,219,335 A | 6/1993 | Willard et al. |
| 5,221,255 A | 6/1993 | Mahurkar et al. |
| 5,222,944 A | 6/1993 | Harris |
| 5,225,369 A | 7/1993 | Su et al. |
| 5,226,899 A | 7/1993 | Lee et al. |
| D338,955 S | 8/1993 | Gresl et al. |
| 5,234,410 A | 8/1993 | Graham et al. |
| 5,242,411 A | 9/1993 | Yamamoto et al. |
| 5,246,426 A | 9/1993 | Lewis et al. |
| 5,246,430 A | 9/1993 | MacFarlane |
| 5,254,107 A | 10/1993 | Soltesz |
| 5,257,980 A | 11/1993 | Van Antwerp et al. |
| 5,267,982 A | 12/1993 | Sylvanowicz |
| 5,269,771 A | 12/1993 | Thomas et al. |
| D345,419 S | 3/1994 | Horrigan et al. |
| 5,290,310 A | 3/1994 | Makower et al. |
| 5,297,546 A | 3/1994 | Spofford et al. |
| 5,312,359 A | 5/1994 | Wallace |
| 5,312,361 A | 5/1994 | Zadini et al. |
| 5,312,363 A | 5/1994 | Ryan et al. |
| 5,318,541 A * | 6/1994 | Viera ............... A61M 25/09041 604/159 |
| 5,320,608 A | 6/1994 | Gerrone |
| 5,322,517 A | 6/1994 | Sircom et al. |
| 5,330,435 A | 7/1994 | Vaillancourt |
| 5,334,159 A | 8/1994 | Turkel |
| 5,338,311 A | 8/1994 | Mahurkar |
| 5,352,205 A | 10/1994 | Dales et al. |
| 5,358,796 A | 10/1994 | Nakamura et al. |
| 5,366,441 A | 11/1994 | Crawford |
| 5,368,661 A | 11/1994 | Nakamura et al. |
| D353,668 S | 12/1994 | Banks et al. |
| 5,376,082 A | 12/1994 | Phelps |
| 5,376,094 A | 12/1994 | Kline |
| 5,380,290 A | 1/1995 | Makower et al. |
| 5,380,292 A | 1/1995 | Wilson |
| 5,395,341 A | 3/1995 | Slater |
| 5,397,311 A | 3/1995 | Walker et al. |
| 5,405,323 A | 4/1995 | Rogers et al. |
| 5,415,177 A | 5/1995 | Zadini et al. |
| 5,415,645 A | 5/1995 | Friend et al. |
| 5,419,766 A | 5/1995 | Chang et al. |
| 5,419,777 A | 5/1995 | Hofling |
| 5,423,760 A | 6/1995 | Yoon |
| 5,425,718 A | 6/1995 | Tay et al. |
| 5,431,506 A | 7/1995 | Masunaga |
| 5,439,449 A | 8/1995 | Mapes et al. |
| 5,445,625 A | 8/1995 | Voda |
| 5,454,785 A | 10/1995 | Smith |
| 5,454,790 A | 10/1995 | Dubrul |
| 5,456,258 A | 10/1995 | Kondo et al. |
| 5,456,668 A | 10/1995 | Ogle, II |
| 5,458,658 A | 10/1995 | Sircom |
| 5,466,230 A | 11/1995 | Davila |
| 5,480,389 A | 1/1996 | McWha et al. |
| 5,482,395 A | 1/1996 | Gasparini |
| 5,484,419 A | 1/1996 | Fleck |
| 5,487,734 A | 1/1996 | Thorne et al. |
| 5,489,273 A | 2/1996 | Whitney et al. |
| 5,496,281 A | 3/1996 | Krebs |
| 5,501,671 A | 3/1996 | Rosen et al. |
| 5,501,675 A | 3/1996 | Erskine |
| 5,507,300 A | 4/1996 | Mukai et al. |
| 5,512,052 A | 4/1996 | Jesch |
| 5,514,108 A | 5/1996 | Stevens |
| 5,520,655 A | 5/1996 | Davila et al. |
| 5,520,657 A | 5/1996 | Sellers et al. |
| D371,195 S | 6/1996 | Krebs |
| 5,522,807 A | 6/1996 | Luther |
| 5,527,290 A | 6/1996 | Zadini et al. |
| 5,527,291 A | 6/1996 | Zadini et al. |
| 5,531,701 A | 7/1996 | Luther |
| 5,531,713 A | 7/1996 | Mastronardi et al. |
| 5,533,988 A | 7/1996 | Dickerson et al. |
| 5,535,785 A | 7/1996 | Werge et al. |
| 5,542,933 A | 8/1996 | Marks |
| 5,554,136 A | 9/1996 | Luther |
| 5,562,629 A | 10/1996 | Haughton et al. |
| 5,562,630 A | 10/1996 | Nichols |
| 5,562,631 A | 10/1996 | Bogert |
| 5,562,633 A | 10/1996 | Wozencroft |
| 5,562,634 A | 10/1996 | Flumene et al. |
| 5,569,202 A | 10/1996 | Kovalic et al. |
| 5,569,217 A | 10/1996 | Luther |
| 5,571,073 A | 11/1996 | Castillo |
| 5,573,510 A | 11/1996 | Isaacson |
| 5,575,777 A | 11/1996 | Cover et al. |
| 5,591,194 A | 1/1997 | Berthiaume |
| 5,599,291 A | 2/1997 | Balbierz et al. |
| 5,599,327 A | 2/1997 | Sugahara et al. |
| 5,609,583 A | 3/1997 | Hakki et al. |
| 5,613,663 A | 3/1997 | Schmidt et al. |
| 5,613,954 A | 3/1997 | Nelson et al. |
| 5,630,802 A | 5/1997 | Moellmann et al. |
| 5,630,823 A | 5/1997 | Schmitz-Rode et al. |
| 5,634,475 A | 6/1997 | Wolvek |
| 5,634,913 A | 6/1997 | Stinger |
| 5,637,091 A | 6/1997 | Hakky et al. |
| 5,645,076 A | 7/1997 | Yoon |
| 5,651,772 A | 7/1997 | Arnett |
| D383,538 S | 9/1997 | Erskine et al. |
| 5,662,622 A | 9/1997 | Gore et al. |
| 5,674,241 A | 10/1997 | Bley et al. |
| 5,676,658 A | 10/1997 | Erskine |
| 5,683,368 A | 11/1997 | Schmidt |
| 5,683,370 A | 11/1997 | Luther et al. |
| 5,685,855 A | 11/1997 | Erskine |
| 5,685,858 A | 11/1997 | Kawand |
| 5,685,860 A | 11/1997 | Chang et al. |
| 5,688,249 A | 11/1997 | Chang et al. |
| 5,693,025 A | 12/1997 | Stevens |
| 5,695,474 A | 12/1997 | Daugherty |
| 5,697,914 A | 12/1997 | Brimhall |
| 5,700,250 A | 12/1997 | Erskine |
| 5,702,367 A | 12/1997 | Cover et al. |
| 5,702,369 A | 12/1997 | Mercereau |
| 5,704,914 A * | 1/1998 | Stocking ........... A61M 25/0631 604/195 |
| 5,722,425 A * | 3/1998 | Bostrom ................ A61N 1/056 600/585 |
| 5,725,503 A | 3/1998 | Arnett |
| 5,730,150 A | 3/1998 | Peppel et al. |
| 5,730,733 A | 3/1998 | Mortier et al. |
| 5,730,741 A | 3/1998 | Horzewski et al. |
| 5,738,144 A | 4/1998 | Rogers |
| 5,738,660 A | 4/1998 | Luther |
| 5,743,882 A | 4/1998 | Luther |
| 5,743,888 A | 4/1998 | Wilkes et al. |
| 5,749,371 A | 5/1998 | Zadini et al. |
| 5,749,857 A | 5/1998 | Cuppy |
| 5,749,861 A | 5/1998 | Guala et al. |
| 5,750,741 A | 5/1998 | Crocker et al. |
| 5,755,693 A | 5/1998 | Walker et al. |
| 5,755,709 A | 5/1998 | Cuppy |
| 5,762,630 A | 6/1998 | Bley et al. |
| 5,762,636 A | 6/1998 | Rupp et al. |
| 5,765,682 A | 6/1998 | Bley et al. |

(56) References Cited

U.S. PATENT DOCUMENTS

| | | |
|---|---|---|
| 5,779,679 A | 7/1998 | Shaw |
| 5,779,680 A | 7/1998 | Yoon |
| 5,779,681 A | 7/1998 | Bonn |
| 5,782,807 A | 7/1998 | Falvai et al. |
| D397,434 S | 8/1998 | Pike |
| 5,792,124 A | 8/1998 | Horrigan et al. |
| 5,800,395 A | 9/1998 | Botich et al. |
| 5,807,339 A | 9/1998 | Bostrom et al. |
| 5,807,342 A | 9/1998 | Musgrave et al. |
| 5,807,350 A | 9/1998 | Diaz |
| 5,810,780 A | 9/1998 | Brimhall et al. |
| 5,810,835 A | 9/1998 | Ryan et al. |
| 5,813,411 A | 9/1998 | Van Bladel et al. |
| 5,817,058 A | 10/1998 | Shaw |
| 5,817,069 A | 10/1998 | Arnett |
| 5,824,001 A | 10/1998 | Erskine |
| 5,827,202 A | 10/1998 | Miraki et al. |
| 5,827,221 A | 10/1998 | Phelps |
| 5,827,227 A | 10/1998 | DeLago |
| 5,830,190 A | 11/1998 | Howell |
| 5,830,224 A | 11/1998 | Cohn et al. |
| 5,839,470 A | 11/1998 | Hiejima et al. |
| 5,843,002 A | 12/1998 | Pecor et al. |
| 5,843,038 A | 12/1998 | Bailey |
| 5,846,259 A | 12/1998 | Berthiaume |
| 5,851,196 A | 12/1998 | Arnett |
| 5,853,393 A | 12/1998 | Bogert |
| 5,855,615 A | 1/1999 | Bley et al. |
| 5,858,002 A | 1/1999 | Jesch |
| 5,865,806 A | 2/1999 | Howell |
| 5,873,864 A | 2/1999 | Luther et al. |
| 5,879,332 A | 3/1999 | Schwemberger et al. |
| 5,879,337 A | 3/1999 | Kuracina et al. |
| 5,885,217 A | 3/1999 | Gisselberg et al. |
| 5,885,251 A | 3/1999 | Luther |
| 5,891,098 A | 4/1999 | Huang |
| 5,891,105 A | 4/1999 | Mahurkar |
| 5,895,398 A | 4/1999 | Wensel et al. |
| 5,902,274 A | 5/1999 | Yamamoto et al. |
| 5,902,832 A | 5/1999 | Van Bladel et al. |
| 5,911,705 A | 6/1999 | Howell |
| 5,911,710 A | 6/1999 | Barry et al. |
| 5,913,848 A | 6/1999 | Luther et al. |
| 5,916,208 A | 6/1999 | Luther et al. |
| 5,928,199 A | 7/1999 | Nakagami |
| D413,382 S | 8/1999 | Maissami |
| 5,935,110 A | 8/1999 | Brimhall |
| 5,941,854 A | 8/1999 | Bhitiyakul |
| 5,944,690 A | 8/1999 | Falwell et al. |
| 5,947,930 A | 9/1999 | Schwemberger et al. |
| 5,951,520 A | 9/1999 | Burzynski et al. |
| 5,954,698 A | 9/1999 | Pike |
| 5,957,893 A | 9/1999 | Luther et al. |
| 5,964,744 A | 10/1999 | Balbierz et al. |
| 5,967,490 A | 10/1999 | Pike |
| 5,984,895 A | 11/1999 | Padilla et al. |
| 5,984,903 A | 11/1999 | Nadal |
| 5,989,220 A | 11/1999 | Shaw et al. |
| 5,989,271 A | 11/1999 | Bonnette et al. |
| 5,997,507 A | 12/1999 | Dysarz |
| 5,997,510 A | 12/1999 | Schwemberger |
| 6,001,080 A | 12/1999 | Kuracina et al. |
| 6,004,278 A | 12/1999 | Botich et al. |
| 6,004,294 A | 12/1999 | Brimhall et al. |
| 6,004,295 A | 12/1999 | Langer et al. |
| 6,011,988 A | 1/2000 | Lynch et al. |
| 6,019,736 A | 2/2000 | Avellanet et al. |
| 6,022,319 A | 2/2000 | Willard et al. |
| 6,024,727 A | 2/2000 | Thorne et al. |
| 6,024,729 A | 2/2000 | Dehdashtian et al. |
| 6,045,734 A | 4/2000 | Luther et al. |
| 6,056,726 A | 5/2000 | Isaacson |
| 6,059,484 A | 5/2000 | Greive |
| 6,066,100 A | 5/2000 | Willard et al. |
| 6,074,378 A | 6/2000 | Mouri et al. |
| 6,077,244 A | 6/2000 | Botich et al. |
| 6,080,137 A | 6/2000 | Pike |
| 6,083,237 A | 7/2000 | Huitema et al. |
| 6,096,004 A | 8/2000 | Meglan et al. |
| 6,096,005 A | 8/2000 | Botich et al. |
| 6,109,264 A | 8/2000 | Sauer |
| 6,117,108 A | 9/2000 | Woehr et al. |
| 6,120,494 A | 9/2000 | Jonkman |
| 6,126,633 A | 10/2000 | Kaji et al. |
| 6,126,641 A | 10/2000 | Shields |
| 6,139,532 A | 10/2000 | Howell et al. |
| 6,139,557 A | 10/2000 | Passafaro et al. |
| 6,159,179 A | 12/2000 | Simonson |
| 6,171,234 B1 * | 1/2001 | White ............ A61M 25/09041 600/102 |
| 6,171,287 B1 | 1/2001 | Lynn et al. |
| 6,176,842 B1 | 1/2001 | Tachibana et al. |
| 6,193,690 B1 | 2/2001 | Dysarz |
| 6,197,001 B1 | 3/2001 | Wilson et al. |
| 6,197,007 B1 | 3/2001 | Thorne et al. |
| 6,197,041 B1 | 3/2001 | Shichman et al. |
| 6,203,527 B1 | 3/2001 | Zadini et al. |
| 6,213,978 B1 | 4/2001 | Voyten |
| 6,217,558 B1 | 4/2001 | Zadini et al. |
| 6,221,047 B1 | 4/2001 | Greene et al. |
| 6,221,048 B1 | 4/2001 | Phelps |
| 6,221,049 B1 | 4/2001 | Selmon et al. |
| 6,224,569 B1 | 5/2001 | Brimhall |
| 6,228,060 B1 | 5/2001 | Howell |
| 6,228,062 B1 | 5/2001 | Howell et al. |
| 6,228,073 B1 | 5/2001 | Noone et al. |
| 6,245,045 B1 | 6/2001 | Stratienko |
| 6,251,092 B1 | 6/2001 | Qin et al. |
| 6,268,399 B1 | 7/2001 | Hultine et al. |
| 6,270,480 B1 | 8/2001 | Dorr et al. |
| 6,273,871 B1 | 8/2001 | Davis et al. |
| 6,280,419 B1 | 8/2001 | Vojtasek |
| 6,287,278 B1 | 9/2001 | Woehr et al. |
| 6,309,379 B1 | 10/2001 | Willard et al. |
| 6,319,244 B2 | 11/2001 | Suresh et al. |
| 6,322,537 B1 | 11/2001 | Chang |
| D452,003 S | 12/2001 | Niermann |
| 6,325,781 B1 | 12/2001 | Takagi et al. |
| 6,325,797 B1 | 12/2001 | Stewart et al. |
| 6,336,914 B1 | 1/2002 | Gillespie, III |
| 6,352,520 B1 | 3/2002 | Miyazaki |
| 6,368,337 B1 | 4/2002 | Kieturakis et al. |
| 6,379,333 B1 | 4/2002 | Brimhall et al. |
| 6,379,372 B1 | 4/2002 | Dehdashtian et al. |
| D457,955 S | 5/2002 | Bilitz |
| 6,406,442 B1 | 6/2002 | McFann et al. |
| D460,179 S | 7/2002 | Isoda et al. |
| 6,422,989 B1 | 7/2002 | Hektner |
| 6,436,070 B1 | 8/2002 | Botich et al. |
| 6,436,112 B2 | 8/2002 | Wensel et al. |
| 6,443,929 B1 | 9/2002 | Kuracina et al. |
| 6,451,052 B1 | 9/2002 | Burmeister et al. |
| 6,461,362 B1 | 10/2002 | Halseth et al. |
| 6,475,217 B1 | 11/2002 | Platt |
| 6,478,779 B1 | 11/2002 | Hu |
| 6,485,473 B1 | 11/2002 | Lynn |
| 6,485,497 B2 | 11/2002 | Wensel et al. |
| 6,497,681 B1 | 12/2002 | Brenner |
| 6,506,181 B2 | 1/2003 | Meng et al. |
| 6,514,236 B1 | 2/2003 | Stratienko |
| 6,524,276 B1 | 2/2003 | Halseth et al. |
| D471,980 S | 3/2003 | Caizza |
| 6,527,759 B1 | 3/2003 | Tachibana et al. |
| 6,530,913 B1 | 3/2003 | Giba et al. |
| 6,530,935 B2 | 3/2003 | Wensel et al. |
| 6,540,725 B1 | 4/2003 | Ponzi |
| 6,540,732 B1 | 4/2003 | Botich et al. |
| 6,544,239 B2 | 4/2003 | Kinsey et al. |
| 6,547,762 B1 * | 4/2003 | Botich ............ A61M 25/09041 604/110 |
| 6,558,355 B1 | 5/2003 | Metzger et al. |
| 6,582,402 B1 | 6/2003 | Erskine |
| 6,582,440 B1 | 6/2003 | Brumbach |
| 6,585,703 B1 | 7/2003 | Kassel et al. |

(56) References Cited

U.S. PATENT DOCUMENTS

| | | |
|---|---|---|
| 6,589,262 B1 | 7/2003 | Honebrink et al. |
| 6,595,955 B2 | 7/2003 | Ferguson et al. |
| 6,595,959 B1 | 7/2003 | Stratienko |
| 6,599,296 B1 | 7/2003 | Gillick et al. |
| 6,607,511 B2 | 8/2003 | Halseth et al. |
| 6,616,630 B1 | 9/2003 | Woehr et al. |
| 6,620,136 B1 | 9/2003 | Pressly, Sr. et al. |
| 6,623,449 B2 | 9/2003 | Paskar |
| 6,623,456 B1 | 9/2003 | Holdaway et al. |
| 6,626,868 B1 | 9/2003 | Prestidge et al. |
| 6,626,869 B1 | 9/2003 | Bint |
| 6,629,959 B2 | 10/2003 | Kuracina et al. |
| 6,632,201 B1 | 10/2003 | Mathias et al. |
| 6,638,252 B2 | 10/2003 | Moulton et al. |
| 6,641,564 B1 | 11/2003 | Kraus |
| 6,645,178 B1 | 11/2003 | Junker et al. |
| 6,652,486 B2 | 11/2003 | Bialecki et al. |
| 6,652,490 B2 | 11/2003 | Howell |
| 6,663,577 B2 | 12/2003 | Jen et al. |
| 6,663,592 B2 | 12/2003 | Rhad et al. |
| 6,666,865 B2 | 12/2003 | Platt |
| 6,679,900 B2 | 1/2004 | Kieturakis et al. |
| 6,689,102 B2 | 2/2004 | Greene |
| 6,692,508 B2 | 2/2004 | Wensel et al. |
| 6,692,509 B2 | 2/2004 | Wensel et al. |
| 6,695,814 B2 | 2/2004 | Greene et al. |
| 6,695,856 B2 | 2/2004 | Kieturakis et al. |
| 6,695,860 B1 | 2/2004 | Ward et al. |
| 6,699,221 B2 | 3/2004 | Vaillancourt |
| 6,702,811 B2 | 3/2004 | Stewart et al. |
| 6,706,018 B2 | 3/2004 | Westlund et al. |
| 6,711,444 B2 | 3/2004 | Koblish |
| 6,712,790 B1 | 3/2004 | Prestidge et al. |
| 6,712,797 B1 | 3/2004 | Southern, Jr. |
| 6,716,197 B2 | 4/2004 | Svendsen |
| 6,730,062 B2 | 5/2004 | Hoffman et al. |
| 6,740,063 B2 | 5/2004 | Lynn |
| 6,740,096 B2 | 5/2004 | Teague et al. |
| 6,745,080 B2 | 6/2004 | Koblish |
| 6,749,588 B1 | 6/2004 | Howell et al. |
| 6,764,468 B1 | 7/2004 | East |
| D494,270 S | 8/2004 | Reschke |
| 6,776,788 B1 | 8/2004 | Klint et al. |
| 6,796,962 B2 | 9/2004 | Ferguson et al. |
| 6,824,545 B2 | 11/2004 | Sepetka et al. |
| 6,832,715 B2 | 12/2004 | Eungard et al. |
| 6,835,190 B2 | 12/2004 | Nguyen |
| 6,837,867 B2 | 1/2005 | Kortelling |
| 6,860,871 B2 | 3/2005 | Kuracina et al. |
| 6,872,193 B2 | 3/2005 | Shaw et al. |
| 6,887,220 B2 | 5/2005 | Hogendijk |
| 6,902,546 B2 | 6/2005 | Ferguson |
| 6,905,483 B2 | 6/2005 | Newby et al. |
| 6,913,595 B2 | 7/2005 | Mastorakis |
| 6,916,311 B2 | 7/2005 | Vojtasek |
| 6,921,386 B2 | 7/2005 | Shue et al. |
| 6,921,391 B1 | 7/2005 | Barker et al. |
| 6,929,624 B1 | 8/2005 | Del Castillo |
| 6,939,325 B2 | 9/2005 | Haining |
| 6,942,652 B1 | 9/2005 | Pressly, Sr. et al. |
| 6,953,448 B2 | 10/2005 | Moulton et al. |
| 6,958,054 B2 | 10/2005 | Fitzgerald |
| 6,958,055 B2 | 10/2005 | Donnan et al. |
| 6,960,191 B2 | 11/2005 | Howlett et al. |
| 6,972,002 B2 | 12/2005 | Thorne |
| 6,974,438 B2 | 12/2005 | Shekalim |
| 6,994,693 B2 | 2/2006 | Tal |
| 7,001,396 B2 | 2/2006 | Glazier et al. |
| 7,004,927 B2 | 2/2006 | Ferguson et al. |
| 7,008,404 B2 | 3/2006 | Nakajima |
| 7,018,372 B2 | 3/2006 | Casey et al. |
| 7,018,390 B2 | 3/2006 | Turovskiy et al. |
| 7,025,746 B2 | 4/2006 | Tal |
| 7,029,467 B2 | 4/2006 | Currier et al. |
| 7,033,335 B2 | 4/2006 | Haarala et al. |
| 7,044,935 B2 | 5/2006 | Shue et al. |
| 7,060,055 B2 | 6/2006 | Wilkinson et al. |
| 7,090,656 B1 | 8/2006 | Botich et al. |
| 7,094,243 B2 | 8/2006 | Mulholland et al. |
| 7,097,633 B2 | 8/2006 | Botich et al. |
| 7,125,396 B2 | 10/2006 | Leinsing et al. |
| 7,125,397 B2 | 10/2006 | Woehr et al. |
| 7,141,040 B2 | 11/2006 | Lichtenberg |
| 7,153,276 B2 | 12/2006 | Barker et al. |
| 7,163,520 B2 | 1/2007 | Bernard et al. |
| 7,169,159 B2 | 1/2007 | Green et al. |
| 7,179,244 B2 | 2/2007 | Smith et al. |
| 7,186,239 B2 | 3/2007 | Woehr |
| 7,191,900 B2 | 3/2007 | Opie et al. |
| 7,192,433 B2 | 3/2007 | Osypka et al. |
| 7,204,813 B2 | 4/2007 | Shue et al. |
| 7,214,211 B2 | 5/2007 | Woehr et al. |
| 7,255,685 B2 | 8/2007 | Pressly, Sr. et al. |
| 7,264,613 B2 | 9/2007 | Woehr et al. |
| 7,291,130 B2 | 11/2007 | McGurk |
| 7,303,547 B2 | 12/2007 | Pressly, Sr. et al. |
| 7,303,548 B2 | 12/2007 | Rhad et al. |
| 7,314,462 B2 | 1/2008 | O'Reagan et al. |
| 7,331,966 B2 | 2/2008 | Soma et al. |
| 7,344,516 B2 | 3/2008 | Erskine |
| 7,354,422 B2 | 4/2008 | Riesenberger et al. |
| 7,374,554 B2 | 5/2008 | Menzi et al. |
| 7,381,205 B2 | 6/2008 | Thommen |
| 7,396,346 B2 | 7/2008 | Nakajima |
| 7,413,562 B2 | 8/2008 | Ferguson et al. |
| 7,422,572 B2 | 9/2008 | Popov et al. |
| 7,458,954 B2 | 12/2008 | Ferguson et al. |
| 7,465,294 B1 | 12/2008 | Vladimirsky |
| 7,468,057 B2 | 12/2008 | Ponzi |
| 7,470,254 B2 | 12/2008 | Basta et al. |
| 7,491,176 B2 | 2/2009 | Mann |
| 7,494,010 B2 | 2/2009 | Opie et al. |
| 7,500,965 B2 | 3/2009 | Menzi et al. |
| 7,507,222 B2 | 3/2009 | Cindrich et al. |
| 7,513,887 B2 | 4/2009 | Halseth et al. |
| 7,513,888 B2 | 4/2009 | Sircom et al. |
| 7,524,306 B2 | 4/2009 | Botich et al. |
| 7,530,965 B2 | 5/2009 | Villa et al. |
| 7,534,227 B2 | 5/2009 | Kulli |
| 7,534,231 B2 | 5/2009 | Kuracina et al. |
| 7,544,170 B2 | 6/2009 | Williams et al. |
| 7,556,617 B2 | 7/2009 | Voorhees, Jr. et al. |
| 7,566,323 B2 | 7/2009 | Chang |
| D601,243 S | 9/2009 | Bierman et al. |
| 7,597,681 B2 | 10/2009 | Sutton et al. |
| 7,608,057 B2 | 10/2009 | Woehr et al. |
| D604,839 S | 11/2009 | Crawford et al. |
| 7,611,485 B2 | 11/2009 | Ferguson |
| 7,611,487 B2 | 11/2009 | Woehr et al. |
| 7,611,499 B2 | 11/2009 | Woehr et al. |
| 7,618,395 B2 | 11/2009 | Ferguson |
| 7,625,360 B2 | 12/2009 | Woehr et al. |
| 7,628,769 B2 | 12/2009 | Grandt et al. |
| 7,632,243 B2 | 12/2009 | Bialecki et al. |
| 7,645,263 B2 | 1/2010 | Angel et al. |
| 7,654,988 B2 | 2/2010 | Moulton et al. |
| 7,658,725 B2 | 2/2010 | Bialecki et al. |
| D612,043 S | 3/2010 | Young et al. |
| 7,678,080 B2 | 3/2010 | Shue et al. |
| 7,682,358 B2 | 3/2010 | Gullickson et al. |
| 7,691,088 B2 | 4/2010 | Howell |
| 7,691,090 B2 | 4/2010 | Belley et al. |
| 7,691,093 B2 | 4/2010 | Brimhall |
| 7,695,458 B2 | 4/2010 | Belley et al. |
| 7,699,807 B2 | 4/2010 | Faust et al. |
| D615,197 S | 5/2010 | Koh et al. |
| 7,708,721 B2 | 5/2010 | Khaw |
| 7,713,243 B2 | 5/2010 | Hillman |
| 7,717,875 B2 | 5/2010 | Knudson et al. |
| 7,722,567 B2 | 5/2010 | Tal |
| 7,722,569 B2 | 5/2010 | Soderholm et al. |
| D617,893 S | 6/2010 | Bierman et al. |
| 7,731,687 B2 | 6/2010 | Menzi et al. |
| 7,731,691 B2 | 6/2010 | Cote et al. |

(56) References Cited

U.S. PATENT DOCUMENTS

| | | |
|---|---|---|
| 7,736,332 B2 | 6/2010 | Carlyon et al. |
| 7,736,337 B2 | 6/2010 | Diep et al. |
| 7,736,339 B2 | 6/2010 | Woehr et al. |
| 7,736,342 B2 | 6/2010 | Abriles et al. |
| 7,740,615 B2 | 6/2010 | Shaw et al. |
| 7,744,574 B2 | 6/2010 | Pederson et al. |
| 7,753,877 B2 | 7/2010 | Bialecki et al. |
| 7,753,887 B2 | 7/2010 | Botich et al. |
| 7,762,984 B2 | 7/2010 | Kumoyama et al. |
| 7,762,993 B2 | 7/2010 | Perez |
| 7,766,879 B2 | 8/2010 | Tan et al. |
| 7,776,052 B2 | 8/2010 | Greenberg et al. |
| 7,785,296 B2 | 8/2010 | Muskatello et al. |
| 7,794,424 B2 | 9/2010 | Paskar |
| 7,798,994 B2 | 9/2010 | Brimhall |
| 7,803,142 B2 | 9/2010 | Longson et al. |
| 7,828,773 B2 | 11/2010 | Swisher et al. |
| 7,828,774 B2 | 11/2010 | Harding et al. |
| 7,833,201 B2 | 11/2010 | Carlyon et al. |
| 7,850,644 B2 | 12/2010 | Gonzalez et al. |
| 7,857,770 B2 | 12/2010 | Raulerson et al. |
| D634,843 S | 3/2011 | Kim et al. |
| 7,896,862 B2 | 3/2011 | Long et al. |
| 7,905,857 B2 | 3/2011 | Swisher |
| 7,914,488 B2 | 3/2011 | Dickerson |
| 7,914,492 B2 | 3/2011 | Heuser |
| 7,922,696 B2 | 4/2011 | Tal et al. |
| 7,922,698 B2 | 4/2011 | Riesenberger et al. |
| 7,927,314 B2 | 4/2011 | Kuracina et al. |
| 7,935,080 B2 | 5/2011 | Howell et al. |
| 7,959,613 B2 | 6/2011 | Rhad et al. |
| 7,972,313 B2 | 7/2011 | Woehr et al. |
| 7,972,324 B2 | 7/2011 | Quint |
| D643,531 S | 8/2011 | van der Weiden |
| 8,029,470 B2 | 10/2011 | Whiting et al. |
| 8,029,472 B2 | 10/2011 | Leinsing et al. |
| 8,048,031 B2 | 11/2011 | Shaw et al. |
| 8,048,039 B2 | 11/2011 | Carlyon et al. |
| 8,057,404 B2 | 11/2011 | Fujiwara et al. |
| 8,062,261 B2 | 11/2011 | Adams |
| 8,075,529 B2 | 12/2011 | Nakajima et al. |
| 8,079,979 B2 | 12/2011 | Moorehead |
| D653,329 S | 1/2012 | Lee-Sepsick |
| 8,100,858 B2 | 1/2012 | Woehr et al. |
| 8,105,286 B2 | 1/2012 | Anderson et al. |
| 8,105,315 B2 | 1/2012 | Johnson et al. |
| 8,123,727 B2 | 2/2012 | Luther et al. |
| 8,152,758 B2 | 4/2012 | Chan et al. |
| 8,162,881 B2 | 4/2012 | Lilley, Jr. et al. |
| 8,167,851 B2 | 5/2012 | Sen |
| 8,177,753 B2 | 5/2012 | Vitullo et al. |
| RE43,473 E | 6/2012 | Newby et al. |
| 8,192,402 B2 | 6/2012 | Anderson et al. |
| 8,202,251 B2 | 6/2012 | Bierman et al. |
| 8,202,253 B1 | 6/2012 | Wexler |
| 8,206,343 B2 | 6/2012 | Racz |
| 8,211,070 B2 | 7/2012 | Woehr et al. |
| 8,221,387 B2 | 7/2012 | Shelso et al. |
| 8,226,612 B2 | 7/2012 | Nakajima |
| 8,235,945 B2 | 8/2012 | Baid |
| 8,251,923 B2 | 8/2012 | Carrez et al. |
| 8,251,950 B2 | 8/2012 | Albert et al. |
| D667,111 S | 9/2012 | Robinson |
| 8,257,322 B2 | 9/2012 | Koehler et al. |
| 8,273,054 B2 | 9/2012 | St. Germain et al. |
| 8,286,657 B2 | 10/2012 | Belley et al. |
| 8,298,186 B2 | 10/2012 | Popov |
| 8,303,543 B2 | 11/2012 | Abulhaj |
| 8,308,685 B2 | 11/2012 | Botich et al. |
| 8,308,691 B2 | 11/2012 | Woehr et al. |
| D672,456 S | 12/2012 | Lee-Sepsick |
| 8,323,249 B2 | 12/2012 | White et al. |
| 8,328,762 B2 | 12/2012 | Woehr et al. |
| 8,328,837 B2 | 12/2012 | Binmoeller |
| 8,333,735 B2 | 12/2012 | Woehr et al. |
| 8,337,424 B2 | 12/2012 | Palmer et al. |
| 8,337,463 B2 | 12/2012 | Woehr et al. |
| 8,337,471 B2 | 12/2012 | Baid |
| D675,318 S | 1/2013 | Luk et al. |
| 8,361,020 B2 | 1/2013 | Stout |
| 8,361,038 B2 | 1/2013 | McKinnon et al. |
| 8,376,994 B2 | 2/2013 | Woehr et al. |
| 8,377,006 B2 | 2/2013 | Tal et al. |
| 8,382,721 B2 | 2/2013 | Woehr et al. |
| 8,388,583 B2 | 3/2013 | Stout et al. |
| 8,403,886 B2 | 3/2013 | Bialecki et al. |
| 8,412,300 B2 | 4/2013 | Sonderegger |
| 8,414,539 B1 | 4/2013 | Kuracina et al. |
| 8,419,688 B2 | 4/2013 | Woehr et al. |
| 8,444,605 B2 | 5/2013 | Kuracina et al. |
| 8,454,536 B2 | 6/2013 | Raulerson et al. |
| 8,460,247 B2 | 6/2013 | Woehr et al. |
| 8,469,928 B2 | 6/2013 | Stout et al. |
| 8,496,628 B2 | 7/2013 | Erskine |
| D687,548 S | 8/2013 | Hayashi |
| 8,506,533 B2 | 8/2013 | Carlyon et al. |
| 8,509,340 B2 | 8/2013 | Michelitsch |
| 8,517,959 B2 | 8/2013 | Kurosawa et al. |
| 8,529,515 B2 | 9/2013 | Woehr et al. |
| 8,535,271 B2 | 9/2013 | Fuchs et al. |
| 8,540,728 B2 | 9/2013 | Woehr et al. |
| 8,545,454 B2 | 10/2013 | Kuracina et al. |
| 8,568,372 B2 | 10/2013 | Woehr et al. |
| 8,574,203 B2 | 11/2013 | Stout et al. |
| 8,579,881 B2 | 11/2013 | Agro et al. |
| 8,585,651 B2 | 11/2013 | Asai |
| 8,585,660 B2 | 11/2013 | Murphy |
| 8,591,467 B2 | 11/2013 | Walker et al. |
| 8,591,468 B2 | 11/2013 | Woehr et al. |
| 8,597,249 B2 | 12/2013 | Woehr et al. |
| 8,622,931 B2 | 1/2014 | Teague et al. |
| 8,622,958 B2 | 1/2014 | Jones et al. |
| 8,622,972 B2 | 1/2014 | Nystrom et al. |
| D700,318 S | 2/2014 | Amoah et al. |
| 8,647,301 B2 | 2/2014 | Bialecki et al. |
| 8,647,313 B2 | 2/2014 | Woehr et al. |
| 8,647,324 B2 | 2/2014 | DeLegge et al. |
| 8,652,104 B2 | 2/2014 | Goral et al. |
| 8,657,790 B2 | 2/2014 | Tal et al. |
| 8,672,888 B2 | 3/2014 | Tal |
| 8,679,063 B2 | 3/2014 | Stout et al. |
| 8,690,833 B2 | 4/2014 | Belson |
| 8,715,242 B2 | 5/2014 | Helm, Jr. |
| 8,721,546 B2 | 5/2014 | Belson |
| 8,728,030 B2 | 5/2014 | Woehr |
| 8,728,035 B2 | 5/2014 | Warring et al. |
| 8,740,859 B2 | 6/2014 | McKinnon et al. |
| 8,740,964 B2 | 6/2014 | Hartley |
| 8,747,387 B2 | 6/2014 | Belley et al. |
| 8,753,317 B2 | 6/2014 | Osborne et al. |
| 8,764,711 B2 | 7/2014 | Kuracina et al. |
| D710,495 S | 8/2014 | Wu et al. |
| 8,814,833 B2 | 8/2014 | Farrell et al. |
| D713,957 S | 9/2014 | Woehr et al. |
| D714,436 S | 9/2014 | Lee-Sepsick |
| 8,827,965 B2 | 9/2014 | Woehr et al. |
| 8,845,584 B2 | 9/2014 | Ferguson et al. |
| D715,931 S | 10/2014 | Watanabe et al. |
| 8,864,714 B2 | 10/2014 | Harding et al. |
| 8,900,192 B2 | 12/2014 | Anderson et al. |
| 8,932,257 B2 | 1/2015 | Woehr |
| 8,932,258 B2 | 1/2015 | Blanchard et al. |
| 8,932,259 B2 | 1/2015 | Stout et al. |
| 8,945,011 B2 | 2/2015 | Sheldon et al. |
| 8,951,230 B2 | 2/2015 | Tanabe et al. |
| 8,956,327 B2 | 2/2015 | Bierman et al. |
| 8,974,426 B2 | 3/2015 | Corcoran et al. |
| 8,979,802 B2 | 3/2015 | Woehr |
| 8,986,227 B2 | 3/2015 | Belson |
| D726,908 S | 4/2015 | Yu et al. |
| 8,998,852 B2 | 4/2015 | Blanchard et al. |
| 9,005,169 B2 | 4/2015 | Gravesen et al. |
| 9,011,351 B2 | 4/2015 | Hoshinouchi |
| 9,011,381 B2 | 4/2015 | Yamada et al. |

(56) References Cited

U.S. PATENT DOCUMENTS

| | | | |
|---|---|---|---|
| D728,781 S | 5/2015 | Pierson et al. |
| 9,022,979 B2 | 5/2015 | Woehr |
| 9,033,927 B2 | 5/2015 | Maan et al. |
| D733,289 S | 6/2015 | Blanchard et al. |
| 9,044,583 B2 | 6/2015 | Vaillancourt |
| D735,321 S | 7/2015 | Blanchard |
| 9,089,671 B2 | 7/2015 | Stout et al. |
| 9,089,674 B2 | 7/2015 | Ginn et al. |
| 9,095,683 B2 | 8/2015 | Hall et al. |
| 9,101,746 B2 | 8/2015 | Stout et al. |
| 9,108,021 B2 | 8/2015 | Hyer et al. |
| 9,114,231 B2 | 8/2015 | Woehr et al. |
| 9,114,241 B2 | 8/2015 | Stout et al. |
| 9,126,012 B2 | 9/2015 | McKinnon et al. |
| 9,138,252 B2 | 9/2015 | Bierman et al. |
| 9,138,545 B2 | 9/2015 | Shaw et al. |
| 9,138,559 B2 | 9/2015 | Odland et al. |
| RE45,776 E | 10/2015 | Root et al. |
| D740,410 S | 10/2015 | Korkuch et al. |
| 9,149,625 B2 | 10/2015 | Woehr et al. |
| 9,149,626 B2 | 10/2015 | Woehr et al. |
| 9,155,863 B2 | 10/2015 | Isaacson et al. |
| 9,162,036 B2 | 10/2015 | Caples et al. |
| 9,162,037 B2 | 10/2015 | Belson et al. |
| 9,180,275 B2 | 11/2015 | Helm |
| D746,445 S | 12/2015 | Lazarus |
| 9,205,231 B2 | 12/2015 | Call et al. |
| 9,216,109 B2 | 12/2015 | Badawi et al. |
| 9,220,531 B2 | 12/2015 | Datta et al. |
| 9,220,871 B2 | 12/2015 | Thorne et al. |
| 9,220,882 B2 | 12/2015 | Belley et al. |
| D748,254 S | 1/2016 | Freigang et al. |
| 9,227,038 B2 | 1/2016 | Woehr |
| 9,242,071 B2 | 1/2016 | Morgan et al. |
| 9,242,072 B2 | 1/2016 | Morgan et al. |
| RE45,896 E | 2/2016 | Stout et al. |
| D748,774 S | 2/2016 | Caron |
| D748,777 S | 2/2016 | Uenishi et al. |
| D749,214 S | 2/2016 | Uenishi et al. |
| D749,727 S | 2/2016 | Wapler et al. |
| D751,194 S | 3/2016 | Yu et al. |
| D752,737 S | 3/2016 | Ohashi |
| 9,289,237 B2 | 3/2016 | Woehr et al. |
| 9,308,352 B2 | 4/2016 | Teoh et al. |
| 9,308,354 B2 | 4/2016 | Farrell et al. |
| 9,320,870 B2 | 4/2016 | Woehr |
| D755,368 S | 5/2016 | Efinger et al. |
| 9,352,119 B2 | 5/2016 | Burkholz et al. |
| 9,352,127 B2 | 5/2016 | Yeh et al. |
| 9,352,129 B2 | 5/2016 | Nardeo et al. |
| 9,358,364 B2 | 6/2016 | Isaacson et al. |
| 9,370,641 B2 | 6/2016 | Woehr et al. |
| 9,381,324 B2 | 7/2016 | Fuchs et al. |
| 9,399,116 B2 | 7/2016 | Goral et al. |
| 9,408,569 B2 | 8/2016 | Andreae et al. |
| 9,421,345 B2 | 8/2016 | Woehr et al. |
| 9,427,549 B2 | 8/2016 | Woehr et al. |
| D775,330 S | 12/2016 | Blennow et al. |
| 9,522,254 B2 | 12/2016 | Belson |
| D776,259 S | 1/2017 | Eldredge |
| 9,545,495 B2 | 1/2017 | Goral et al. |
| 9,554,817 B2 | 1/2017 | Goldfarb et al. |
| D779,059 S | 2/2017 | Nino et al. |
| D779,661 S | 2/2017 | McKnight et al. |
| 9,579,486 B2 | 2/2017 | Burkholz et al. |
| 9,586,027 B2 | 3/2017 | Tisci et al. |
| 9,592,367 B2 | 3/2017 | Harding et al. |
| 9,616,201 B2 | 4/2017 | Belson |
| 9,623,210 B2 | 4/2017 | Woehr |
| 9,675,784 B2 | 6/2017 | Belson |
| 9,687,633 B2 | 6/2017 | Teoh |
| D791,311 S | 7/2017 | Yantz |
| 9,707,378 B2 | 7/2017 | Leinsing et al. |
| 9,717,523 B2 | 8/2017 | Feng et al. |
| 9,717,887 B2 | 8/2017 | Tan |
| 9,737,252 B2 | 8/2017 | Teoh et al. |
| 9,750,532 B2 | 9/2017 | Toomey et al. |
| 9,750,928 B2 | 9/2017 | Burkholz et al. |
| 9,757,540 B2 | 9/2017 | Belson |
| 9,764,085 B2 | 9/2017 | Teoh |
| 9,764,117 B2 | 9/2017 | Bierman et al. |
| 9,775,972 B2 | 10/2017 | Christensen et al. |
| 9,782,568 B2 | 10/2017 | Belson |
| 9,789,279 B2 | 10/2017 | Burkholz et al. |
| 9,795,766 B2 | 10/2017 | Teoh |
| 9,844,646 B2 | 12/2017 | Knutsson |
| 9,861,792 B2 | 1/2018 | Hall et al. |
| 9,872,971 B2 | 1/2018 | Blanchard |
| D810,282 S | 2/2018 | Ratjen |
| D815,737 S | 4/2018 | Bergstrom et al. |
| 9,950,139 B2 | 4/2018 | Blanchard et al. |
| 9,962,525 B2 | 5/2018 | Woehr |
| 10,004,878 B2 | 6/2018 | Ishida |
| 10,086,171 B2 | 10/2018 | Belson |
| 10,232,146 B2 | 3/2019 | Braithwaite et al. |
| 10,328,239 B2 | 6/2019 | Belson |
| 10,357,635 B2 | 7/2019 | Korkuch et al. |
| 10,384,039 B2 | 8/2019 | Ribelin et al. |
| 10,426,931 B2 | 10/2019 | Blanchard et al. |
| D870,271 S | 12/2019 | Kheradpir et al. |
| D870,883 S | 12/2019 | Harding et al. |
| 10,493,262 B2 | 12/2019 | Tran et al. |
| 10,525,236 B2 | 1/2020 | Belson |
| 10,688,280 B2 | 6/2020 | Blanchard et al. |
| 10,688,281 B2 | 6/2020 | Blanchard et al. |
| 10,722,685 B2 | 7/2020 | Blanchard et al. |
| 10,806,906 B2 | 10/2020 | Warring et al. |
| 11,389,626 B2 | 7/2022 | Tran et al. |
| 11,400,260 B2 | 8/2022 | Huang et al. |
| 2001/0014786 A1 | 8/2001 | Greene et al. |
| 2001/0020153 A1 | 9/2001 | Howell |
| 2002/0052576 A1 | 5/2002 | Massengale |
| 2002/0077595 A1 | 6/2002 | Hundertmark et al. |
| 2002/0103446 A1 | 8/2002 | McFann et al. |
| 2002/0107526 A1 | 8/2002 | Greenberg et al. |
| 2002/0128604 A1 | 9/2002 | Nakajima |
| 2002/0165497 A1 | 11/2002 | Greene |
| 2002/0177812 A1 | 11/2002 | Moulton et al. |
| 2003/0032922 A1 | 2/2003 | Moorehead |
| 2003/0032936 A1 | 2/2003 | Lederman |
| 2003/0060760 A1 | 3/2003 | Botich et al. |
| 2003/0073956 A1 | 4/2003 | Hoffman et al. |
| 2003/0120214 A1 | 6/2003 | Howell |
| 2003/0153874 A1 | 8/2003 | Tal |
| 2003/0187396 A1 | 10/2003 | Ponzi |
| 2003/0204186 A1 | 10/2003 | Geistert |
| 2004/0019329 A1 | 1/2004 | Erskine |
| 2004/0030291 A1 | 2/2004 | Holdaway et al. |
| 2004/0034383 A1 | 2/2004 | Belson |
| 2004/0044302 A1 | 3/2004 | Bernard et al. |
| 2004/0044313 A1 | 3/2004 | Nakajima |
| 2004/0092879 A1 | 5/2004 | Kraus et al. |
| 2004/0106903 A1 | 6/2004 | Shue et al. |
| 2004/0111059 A1 | 6/2004 | Howlett et al. |
| 2004/0122373 A1 | 6/2004 | Botich et al. |
| 2004/0176758 A1 | 9/2004 | Yassinzadeh |
| 2004/0193118 A1 | 9/2004 | Bergeron |
| 2004/0215146 A1 | 10/2004 | Lampropoulos et al. |
| 2004/0236288 A1 | 11/2004 | Howell et al. |
| 2004/0243061 A1 | 12/2004 | McGurk |
| 2004/0267204 A1 | 12/2004 | Brustowicz |
| 2005/0004524 A1 | 1/2005 | Newby et al. |
| 2005/0004532 A1 | 1/2005 | Woehr et al. |
| 2005/0010095 A1 | 1/2005 | Stewart et al. |
| 2005/0020940 A1 | 1/2005 | Opie et al. |
| 2005/0021002 A1 | 1/2005 | Deckman et al. |
| 2005/0027256 A1 | 2/2005 | Barker et al. |
| 2005/0033137 A1 | 2/2005 | Oral et al. |
| 2005/0040061 A1 | 2/2005 | Opie et al. |
| 2005/0075606 A1* | 4/2005 | Botich .............. A61M 25/0631 |
| | | 604/110 |
| 2005/0107769 A1 | 5/2005 | Thommen |
| 2005/0119619 A1 | 6/2005 | Haining |
| 2005/0131350 A1 | 6/2005 | Shaw et al. |

(56) References Cited

U.S. PATENT DOCUMENTS

| | | |
|---|---|---|
| 2005/0165355 A1 | 7/2005 | Fitzgerald |
| 2005/0197623 A1 | 9/2005 | Leeflang et al. |
| 2005/0245847 A1 | 11/2005 | Schaeffer |
| 2005/0256505 A1 | 11/2005 | Long et al. |
| 2005/0273057 A1 | 12/2005 | Popov |
| 2006/0025721 A1 | 2/2006 | Duffy et al. |
| 2006/0036219 A1 | 2/2006 | Alvin |
| 2006/0079787 A1 | 4/2006 | Whiting et al. |
| 2006/0084964 A1 | 4/2006 | Knudson et al. |
| 2006/0155245 A1 | 7/2006 | Woehr |
| 2006/0161115 A1 | 7/2006 | Fangrow |
| 2006/0167405 A1 | 7/2006 | King et al. |
| 2006/0200080 A1 | 9/2006 | Abulhaj |
| 2006/0229563 A1 | 10/2006 | O'Reagan et al. |
| 2006/0264834 A1 | 11/2006 | Vaillancourt |
| 2006/0264841 A1 | 11/2006 | Cote et al. |
| 2007/0043422 A1 | 2/2007 | Shmulewitz et al. |
| 2007/0060999 A1 | 3/2007 | Randall et al. |
| 2007/0083162 A1 | 4/2007 | O'Reagan et al. |
| 2007/0083188 A1 | 4/2007 | Grandt et al. |
| 2007/0100284 A1 | 5/2007 | Leinsing et al. |
| 2007/0123803 A1 | 5/2007 | Fujiwara et al. |
| 2007/0142779 A1 | 6/2007 | Duane et al. |
| 2007/0179446 A1 | 8/2007 | Carrez et al. |
| 2007/0191777 A1 | 8/2007 | King |
| 2007/0191786 A1 | 8/2007 | Raines et al. |
| 2007/0193903 A1 | 8/2007 | Opie et al. |
| 2007/0225647 A1 | 9/2007 | Luther et al. |
| 2007/0233007 A1 | 10/2007 | Adams |
| 2007/0244438 A1 | 10/2007 | Perez |
| 2007/0255221 A1 | 11/2007 | Nakajima |
| 2007/0276288 A1 | 11/2007 | Khaw |
| 2008/0039796 A1 | 2/2008 | Nakajima |
| 2008/0065011 A1 | 3/2008 | Marchand et al. |
| 2008/0082082 A1 | 4/2008 | Carlyon et al. |
| 2008/0097330 A1 | 4/2008 | King et al. |
| 2008/0108911 A1 | 5/2008 | Palmer et al. |
| 2008/0108944 A1 | 5/2008 | Woehr et al. |
| 2008/0108974 A1 | 5/2008 | Yee Roth |
| 2008/0125709 A1 | 5/2008 | Chang et al. |
| 2008/0131300 A1 | 6/2008 | Junod et al. |
| 2008/0132846 A1 | 6/2008 | Shue et al. |
| 2008/0147010 A1 | 6/2008 | Nakajima et al. |
| 2008/0243165 A1 | 10/2008 | Mauch et al. |
| 2008/0262430 A1 | 10/2008 | Anderson et al. |
| 2008/0262431 A1 | 10/2008 | Anderson et al. |
| 2008/0294111 A1 | 11/2008 | Tal et al. |
| 2008/0300574 A1 | 12/2008 | Belson et al. |
| 2009/0018567 A1 | 1/2009 | Escudero et al. |
| 2009/0030380 A1 | 1/2009 | Binmoeller |
| 2009/0036836 A1 | 2/2009 | Nystrom et al. |
| 2009/0048566 A1 | 2/2009 | Ferguson et al. |
| 2009/0131872 A1 | 5/2009 | Popov |
| 2009/0157006 A1 | 6/2009 | Nardeo et al. |
| 2009/0221961 A1 | 9/2009 | Tal et al. |
| 2009/0227953 A1 | 9/2009 | Tan et al. |
| 2009/0287154 A1 | 11/2009 | Harding et al. |
| 2009/0292243 A1 | 11/2009 | Harding et al. |
| 2009/0299291 A1 | 12/2009 | Baid |
| 2010/0010441 A1 | 1/2010 | Belson |
| 2010/0010447 A1 | 1/2010 | Luther et al. |
| 2010/0016838 A1 | 1/2010 | Butts et al. |
| 2010/0036331 A1 | 2/2010 | Sen |
| 2010/0056910 A1 | 3/2010 | Yanuma |
| 2010/0057183 A1 | 3/2010 | Mangiardi et al. |
| 2010/0087787 A1 | 4/2010 | Woehr et al. |
| 2010/0094116 A1 | 4/2010 | Silverstein |
| 2010/0094310 A1 | 4/2010 | Warring et al. |
| 2010/0137815 A1 | 6/2010 | Kuracina et al. |
| 2010/0168674 A1 | 7/2010 | Shaw et al. |
| 2010/0204654 A1 | 8/2010 | Mulholland et al. |
| 2010/0204660 A1 | 8/2010 | McKinnon et al. |
| 2010/0204675 A1 | 8/2010 | Woehr et al. |
| 2010/0210934 A1 | 8/2010 | Belson |
| 2010/0238705 A1 | 9/2010 | Kim et al. |
| 2010/0246707 A1 | 9/2010 | Michelitsch |
| 2010/0331732 A1 | 12/2010 | Raulerson et al. |
| 2011/0004162 A1 | 1/2011 | Tal |
| 2011/0009827 A1 | 1/2011 | Bierman et al. |
| 2011/0015573 A1 | 1/2011 | Maan et al. |
| 2011/0021994 A1 | 1/2011 | Anderson et al. |
| 2011/0046570 A1 | 2/2011 | Stout et al. |
| 2011/0125097 A1 | 5/2011 | Shaw et al. |
| 2011/0137252 A1 | 6/2011 | Oster et al. |
| 2011/0196315 A1 | 8/2011 | Chappel |
| 2011/0207157 A1 | 8/2011 | Gautier et al. |
| 2011/0218496 A1 | 9/2011 | Bierman |
| 2011/0251559 A1 | 10/2011 | Tal et al. |
| 2011/0276002 A1 | 11/2011 | Bierman |
| 2011/0282285 A1 | 11/2011 | Blanchard et al. |
| 2011/0288482 A1 | 11/2011 | Farrell et al. |
| 2011/0306933 A1 | 12/2011 | Djordjevic et al. |
| 2011/0319838 A1 | 12/2011 | Goral et al. |
| 2012/0053523 A1 | 3/2012 | Harding |
| 2012/0071857 A1 | 3/2012 | Goldfarb et al. |
| 2012/0078231 A1 | 3/2012 | Hoshinouchi |
| 2012/0101440 A1 | 4/2012 | Kamen et al. |
| 2012/0123332 A1 | 5/2012 | Erskine |
| 2012/0123354 A1 | 5/2012 | Woehr |
| 2012/0157854 A1 | 6/2012 | Kurrus et al. |
| 2012/0179104 A1 | 7/2012 | Woehr et al. |
| 2012/0184896 A1 | 7/2012 | DeLegge et al. |
| 2012/0197200 A1 | 8/2012 | Belson |
| 2012/0220942 A1 | 8/2012 | Hall et al. |
| 2012/0220956 A1 | 8/2012 | Kuracina et al. |
| 2012/0259293 A1 | 10/2012 | Bialecki et al. |
| 2012/0271232 A1 | 10/2012 | Katsurada et al. |
| 2012/0296282 A1 | 11/2012 | Koehler et al. |
| 2012/0310179 A1 | 12/2012 | Truitt et al. |
| 2012/0316500 A1 | 12/2012 | Bierman et al. |
| 2012/0323181 A1 | 12/2012 | Shaw et al. |
| 2013/0030391 A1 | 1/2013 | Baid |
| 2013/0158506 A1 | 6/2013 | Harris et al. |
| 2013/0184645 A1 | 7/2013 | Baid |
| 2013/0204206 A1 | 8/2013 | Morgan et al. |
| 2013/0204226 A1 | 8/2013 | Keyser |
| 2013/0218082 A1 | 8/2013 | Hyer et al. |
| 2013/0304030 A1 | 11/2013 | Gray et al. |
| 2013/0310764 A1 | 11/2013 | Burkholz et al. |
| 2013/0324930 A1 | 12/2013 | Fuchs et al. |
| 2014/0012203 A1 | 1/2014 | Woehr et al. |
| 2014/0031752 A1 | 1/2014 | Blanchard et al. |
| 2014/0039461 A1 | 2/2014 | Anderson et al. |
| 2014/0058329 A1 | 2/2014 | Walker et al. |
| 2014/0058336 A1 | 2/2014 | Burkholz et al. |
| 2014/0058357 A1 | 2/2014 | Keyser et al. |
| 2014/0073928 A1 | 3/2014 | Yamashita et al. |
| 2014/0074034 A1 | 3/2014 | Tanabe et al. |
| 2014/0088509 A1 | 3/2014 | Sonderegger et al. |
| 2014/0094774 A1 | 4/2014 | Blanchard |
| 2014/0094836 A1 | 4/2014 | Feng et al. |
| 2014/0114239 A1 | 4/2014 | Dib et al. |
| 2014/0128775 A1 | 5/2014 | Andreae et al. |
| 2014/0135702 A1 | 5/2014 | Woehr et al. |
| 2014/0135703 A1 | 5/2014 | Yeh et al. |
| 2014/0143999 A1 | 5/2014 | Goral et al. |
| 2014/0180250 A1 | 6/2014 | Belson |
| 2014/0188003 A1 | 7/2014 | Belson |
| 2014/0194853 A1 | 7/2014 | Morgan et al. |
| 2014/0214005 A1 | 7/2014 | Belson |
| 2014/0221977 A1 | 8/2014 | Belson |
| 2014/0236099 A1 | 8/2014 | Nakagami et al. |
| 2014/0243734 A1 | 8/2014 | Eubanks et al. |
| 2014/0249488 A1 | 9/2014 | Woehr |
| 2014/0257359 A1 | 9/2014 | Tegels et al. |
| 2014/0276224 A1 | 9/2014 | Ranganathan et al. |
| 2014/0276432 A1 | 9/2014 | Bierman et al. |
| 2014/0276434 A1 | 9/2014 | Woehr et al. |
| 2014/0303561 A1 | 10/2014 | Li |
| 2014/0323988 A1 | 10/2014 | Magnani et al. |
| 2014/0336582 A1 | 11/2014 | Tisci et al. |
| 2014/0357983 A1 | 12/2014 | Toomey et al. |
| 2014/0358123 A1 | 12/2014 | Ueda et al. |
| 2014/0364809 A1 | 12/2014 | Isaacson et al. |

(56) References Cited

U.S. PATENT DOCUMENTS

| | | |
|---|---|---|
| 2014/0371715 A1 | 12/2014 | Farrell et al. |
| 2014/0371720 A1 | 12/2014 | Urmey |
| 2014/0378867 A1 | 12/2014 | Belson |
| 2015/0025467 A1 | 1/2015 | Woehr |
| 2015/0038909 A1 | 2/2015 | Christensen et al. |
| 2015/0038910 A1 | 2/2015 | Harding et al. |
| 2015/0038943 A1 | 2/2015 | Warring et al. |
| 2015/0051584 A1 | 2/2015 | Korkuch et al. |
| 2015/0080801 A1 | 3/2015 | Tanabe et al. |
| 2015/0080810 A1 | 3/2015 | Henderson et al. |
| 2015/0088095 A1 | 3/2015 | Luther et al. |
| 2015/0094659 A1 | 4/2015 | Schraga |
| 2015/0119806 A1 | 4/2015 | Blanchard et al. |
| 2015/0119852 A1 | 4/2015 | Wexler |
| 2015/0126932 A1 | 5/2015 | Knutsson |
| 2015/0151086 A1 | 6/2015 | Teoh |
| 2015/0151088 A1 | 6/2015 | Lim et al. |
| 2015/0190168 A1 | 7/2015 | Bierman et al. |
| 2015/0190570 A1 | 7/2015 | Teoh |
| 2015/0190617 A1 | 7/2015 | Anderson et al. |
| 2015/0202414 A1 | 7/2015 | Hwang |
| 2015/0202421 A1 | 7/2015 | Ma et al. |
| 2015/0224267 A1 | 8/2015 | Farrell et al. |
| 2015/0231364 A1 | 8/2015 | Blanchard et al. |
| 2015/0238705 A1 | 8/2015 | Gravesen et al. |
| 2015/0290431 A1 | 10/2015 | Hall et al. |
| 2015/0306347 A1 | 10/2015 | Yagi |
| 2015/0306356 A1 | 10/2015 | Gill |
| 2015/0328434 A1 | 11/2015 | Gaur |
| 2015/0328438 A1 | 11/2015 | Baid |
| 2015/0335858 A1 | 11/2015 | Woehr et al. |
| 2015/0359473 A1 | 12/2015 | Garrett et al. |
| 2016/0008580 A1 | 1/2016 | Woehr et al. |
| 2016/0015943 A1 | 1/2016 | Belson et al. |
| 2016/0015945 A1 | 1/2016 | Warring et al. |
| 2016/0022312 A1 | 1/2016 | Tang et al. |
| 2016/0022963 A1 | 1/2016 | Belson |
| 2016/0030716 A1 | 2/2016 | Mallin et al. |
| 2016/0045715 A1 | 2/2016 | Galgano et al. |
| 2016/0089513 A1 | 3/2016 | Ishida |
| 2016/0106959 A1 | 4/2016 | Woehr |
| 2016/0114136 A1 | 4/2016 | Woehr |
| 2016/0114137 A1 | 4/2016 | Woehr et al. |
| 2016/0158503 A1 | 6/2016 | Woehr |
| 2016/0158526 A1 | 6/2016 | Woehr |
| 2016/0175563 A1 | 6/2016 | Woehr et al. |
| 2016/0184557 A1 | 6/2016 | Call et al. |
| 2016/0199575 A1 | 7/2016 | Belley et al. |
| 2016/0206852 A1 | 7/2016 | Morgan et al. |
| 2016/0206858 A1 | 7/2016 | Ishida |
| 2016/0220161 A1 | 8/2016 | Goral et al. |
| 2016/0220786 A1 | 8/2016 | Mitchell et al. |
| 2016/0256667 A1 | 9/2016 | Ribelin et al. |
| 2016/0296729 A1 | 10/2016 | Fuchs et al. |
| 2016/0310704 A1 | 10/2016 | Ng et al. |
| 2016/0331937 A1 | 11/2016 | Teoh |
| 2016/0331938 A1 | 11/2016 | Blanchard et al. |
| 2016/0354580 A1 | 12/2016 | Teoh et al. |
| 2016/0361490 A1 | 12/2016 | Phang et al. |
| 2016/0361519 A1 | 12/2016 | Teoh et al. |
| 2017/0000982 A1 | 1/2017 | Ishida |
| 2017/0035992 A1 | 2/2017 | Harding et al. |
| 2017/0043132 A1 | 2/2017 | Ishida |
| 2017/0080205 A1 | 3/2017 | Lauer |
| 2017/0087338 A1 | 3/2017 | Belson |
| 2017/0136217 A1 | 5/2017 | Riesenberger et al. |
| 2017/0203050 A1 | 7/2017 | Bauer et al. |
| 2017/0209668 A1 | 7/2017 | Belson |
| 2017/0246429 A1 | 8/2017 | Tan et al. |
| 2017/0259036 A1 | 9/2017 | Belson |
| 2017/0361071 A1 | 12/2017 | Belson |
| 2018/0028780 A1 | 2/2018 | Blanchard et al. |
| 2018/0071509 A1 | 3/2018 | Tran et al. |
| 2018/0099123 A1 | 4/2018 | Woehr |
| 2018/0126125 A1 | 5/2018 | Hall et al. |
| 2018/0133437 A1 | 5/2018 | Blanchard |
| 2018/0229003 A1 | 8/2018 | Blanchard et al. |
| 2018/0229004 A1 | 8/2018 | Blanchard et al. |
| 2019/0022358 A1 | 1/2019 | Belson |
| 2019/0192829 A1 | 6/2019 | Belson et al. |
| 2019/0201667 A1 | 7/2019 | Braithwaite et al. |
| 2019/0240459 A1 | 8/2019 | Belson |
| 2019/0275303 A1 | 9/2019 | Tran et al. |
| 2019/0307986 A1 | 10/2019 | Belson |
| 2019/0351193 A1 | 11/2019 | Hall |
| 2019/0351196 A1 | 11/2019 | Ribelin et al. |
| 2020/0001051 A1 | 1/2020 | Huang et al. |
| 2020/0094037 A1 | 3/2020 | Tran et al. |
| 2020/0261696 A1 | 8/2020 | Blanchard |
| 2020/0316347 A1 | 10/2020 | Belson |
| 2021/0052858 A1 | 2/2021 | Isaacson et al. |
| 2021/0308428 A1 | 10/2021 | Blanchard et al. |
| 2021/0402155 A1 | 12/2021 | Hall et al. |
| 2022/0362523 A1 | 11/2022 | Huang et al. |
| 2022/0379093 A1 | 12/2022 | Nielson |

FOREIGN PATENT DOCUMENTS

| | | |
|---|---|---|
| CN | 1178707 A | 4/1998 |
| CN | 1319023 A | 10/2001 |
| CN | 1523970 A | 8/2004 |
| CN | 1871043 A | 11/2006 |
| CN | 101242868 A | 8/2008 |
| CN | 101293122 A | 10/2008 |
| CN | 101417159 A | 4/2009 |
| CN | 101784300 A | 7/2010 |
| CN | 102099075 A | 6/2011 |
| CN | 102939129 A | 2/2013 |
| CN | 104689456 A | 6/2015 |
| CN | 105073174 A | 11/2015 |
| CN | 105188826 A | 12/2015 |
| CN | 105705191 A | 6/2016 |
| DE | 20210394 U1 | 9/2002 |
| EP | 0314470 A2 | 5/1989 |
| EP | 417764 A1 | 3/1991 |
| EP | 475857 A1 | 3/1992 |
| EP | 515710 A1 | 12/1992 |
| EP | 567321 A2 | 10/1993 |
| EP | 652020 A2 | 5/1995 |
| EP | 0730880 A1 | 9/1996 |
| EP | 747075 A2 | 12/1996 |
| EP | 750916 A2 | 1/1997 |
| EP | 778043 A1 | 6/1997 |
| EP | 800790 A2 | 10/1997 |
| EP | 832663 A2 | 4/1998 |
| EP | 910988 A1 | 4/1999 |
| EP | 942761 A1 | 9/1999 |
| EP | 1075850 A2 | 2/2001 |
| EP | 1378263 A2 | 1/2004 |
| EP | 1418971 A2 | 5/2004 |
| EP | 1457229 A1 | 9/2004 |
| EP | 1611916 A1 | 1/2006 |
| EP | 1907042 A2 | 4/2008 |
| EP | 1974765 A1 | 10/2008 |
| EP | 2150304 A2 | 2/2010 |
| EP | 2272432 A1 | 1/2011 |
| EP | 2347785 A1 | 7/2011 |
| EP | 2569046 A1 | 3/2013 |
| GB | 2529270 A | 2/2016 |
| JP | 2003-159334 A | 6/2003 |
| JP | 2004-130074 A | 4/2004 |
| JP | 2004-223252 A | 8/2004 |
| JP | 2005-137888 A | 6/2005 |
| JP | 2009-500129 A | 1/2009 |
| JP | 2010-088521 A | 4/2010 |
| JP | 2013-529111 A | 7/2013 |
| JP | 2018-118079 A | 8/2018 |
| JP | 6692869 B2 | 5/2020 |
| WO | 83/01575 A1 | 5/1983 |
| WO | 1992013584 A1 | 8/1992 |
| WO | 92/22344 A1 | 12/1992 |
| WO | 1994006681 A2 | 3/1994 |
| WO | 1995011710 A1 | 5/1995 |
| WO | 95/19193 A1 | 7/1995 |

(56) References Cited

FOREIGN PATENT DOCUMENTS

| | | |
|---|---|---|
| WO | 95/23003 A1 | 8/1995 |
| WO | 96/32981 A1 | 10/1996 |
| WO | 1996040359 A1 | 12/1996 |
| WO | 97/05912 A2 | 2/1997 |
| WO | 97/21458 A1 | 6/1997 |
| WO | 1997045151 A1 | 12/1997 |
| WO | 98/24494 A1 | 6/1998 |
| WO | 1998030268 A1 | 7/1998 |
| WO | 1998053875 A1 | 12/1998 |
| WO | 1999008742 A1 | 2/1999 |
| WO | 1999026682 A1 | 6/1999 |
| WO | 00/06226 A1 | 2/2000 |
| WO | 00/12160 A1 | 3/2000 |
| WO | 2000012167 A1 | 3/2000 |
| WO | 00/47256 A1 | 8/2000 |
| WO | 0067829 A1 | 11/2000 |
| WO | 2001007103 A1 | 2/2001 |
| WO | 01/26725 A1 | 4/2001 |
| WO | 02/41932 A2 | 5/2002 |
| WO | 02/066093 A2 | 8/2002 |
| WO | 02/076526 A2 | 10/2002 |
| WO | 03/11381 A1 | 2/2003 |
| WO | 03/043686 A1 | 5/2003 |
| WO | 03/047675 A2 | 6/2003 |
| WO | 2004/018031 A2 | 3/2004 |
| WO | 2005002659 A1 | 1/2005 |
| WO | 2004106203 A3 | 3/2005 |
| WO | 2005/074412 A2 | 8/2005 |
| WO | 2005/087306 A1 | 9/2005 |
| WO | 2006062996 A2 | 6/2006 |
| WO | 2007006055 A2 | 1/2007 |
| WO | 2007/032343 A1 | 3/2007 |
| WO | 2007094841 A1 | 8/2007 |
| WO | 2007098355 A1 | 8/2007 |
| WO | 2007098359 A1 | 8/2007 |
| WO | 2008005618 A2 | 1/2008 |
| WO | 2008030999 A2 | 3/2008 |
| WO | 2008/131300 A2 | 10/2008 |
| WO | 2008/137956 A2 | 11/2008 |
| WO | 2009/001309 A1 | 12/2008 |
| WO | 2008147600 A1 | 12/2008 |
| WO | 2009031161 A1 | 3/2009 |
| WO | 2009114837 A2 | 9/2009 |
| WO | 2009/124990 A1 | 10/2009 |
| WO | 2010015676 A1 | 2/2010 |
| WO | 2010/048449 A2 | 4/2010 |
| WO | 2010/132608 A2 | 11/2010 |
| WO | 2011036574 A1 | 3/2011 |
| WO | 2011143621 A1 | 11/2011 |
| WO | 2012/037213 A1 | 3/2012 |
| WO | 2012106266 A1 | 8/2012 |
| WO | 2012154277 A1 | 11/2012 |
| WO | 2012166746 A1 | 12/2012 |
| WO | 2012174109 A1 | 12/2012 |
| WO | 2013119557 A1 | 8/2013 |
| WO | 2013126446 A1 | 8/2013 |
| WO | 2013187827 A1 | 12/2013 |
| WO | 2014006403 A1 | 1/2014 |
| WO | 2014029424 A1 | 2/2014 |
| WO | 2014074417 A2 | 5/2014 |
| WO | 2014081942 A1 | 5/2014 |
| WO | 2014/123848 A1 | 8/2014 |
| WO | 2014120741 A1 | 8/2014 |
| WO | 2014133617 A1 | 9/2014 |
| WO | 2014140257 A1 | 9/2014 |
| WO | 2014140265 A1 | 9/2014 |
| WO | 2014/165783 A1 | 10/2014 |
| WO | 2014158908 A1 | 10/2014 |
| WO | 2014182421 A1 | 11/2014 |
| WO | 2014197656 A1 | 12/2014 |
| WO | 2014204593 A1 | 12/2014 |
| WO | 2015017136 A1 | 2/2015 |
| WO | 2015024904 A1 | 2/2015 |
| WO | 2015035393 A1 | 3/2015 |
| WO | 2015058136 A1 | 4/2015 |
| WO | 15108913 A1 | 7/2015 |
| WO | 2015/168655 A2 | 11/2015 |
| WO | 15164912 A1 | 11/2015 |
| WO | 2016/037127 A1 | 3/2016 |
| WO | 16178974 A1 | 11/2016 |
| WO | 2018/049413 A1 | 3/2018 |
| WO | 2018170349 A1 | 9/2018 |
| WO | 2019173641 A1 | 9/2019 |

OTHER PUBLICATIONS

U.S. Appl. No. 14/099,050, filed Dec. 6, 2013 Final Office Action dated Jan. 30, 2017.
U.S. Appl. No. 14/099,050, filed Dec. 6, 2013 Non-Final Office Action dated Dec. 22, 2015.
U.S. Appl. No. 14/099,050, filed Dec. 6, 2013 Non-Final Office Action dated Jul. 19, 2016.
U.S. Appl. No. 14/099,050, filed Dec. 6, 2013 Notice of Allowance dated Sep. 14, 2017.
U.S. Appl. No. 14/099,050, filed Dec. 6, 2013 Notice of Panel Decision dated Aug. 1, 2017.
U.S. Appl. No. 14/167,149, filed Jan. 29, 2014 Non-Final Office Action dated Oct. 21, 2015.
U.S. Appl. No. 14/167,149, filed Jan. 29, 2014 Notice of Allowance dated Jul. 6, 2016.
U.S. Appl. No. 14/174,071, filed Feb. 6, 2014 Final Office Action dated Dec. 2, 2016.
U.S. Appl. No. 14/174,071, filed Feb. 6, 2014 Non-Final Office Action dated Jul. 29, 2016.
U.S. Appl. No. 14/174,071, filed Feb. 6, 2014 Non-Final Office Action dated Mar. 31, 2016.
U.S. Appl. No. 14/192,541, filed Feb. 27, 2014 Non-Final Office Action dated Jul. 20, 2016.
U.S. Appl. No. 14/192,541, filed Feb. 27, 2014 Notice of Allowance dated Dec. 6, 2016.
U.S. Appl. No. 14/192,541, filed Feb. 27, 2014 Notice of Corrected Allowability dated Mar. 8, 2017.
U.S. Appl. No. 14/250,093, filed Apr. 10, 2014 Advisory Action dated May 19, 2017.
U.S. Appl. No. 14/250,093, filed Apr. 10, 2014 Examiner's Answer dated Jun. 20, 2018.
U.S. Appl. No. 14/250,093, filed Apr. 10, 2014 Final Office Action dated Mar. 9, 2017.
U.S. Appl. No. 14/250,093, filed Apr. 10, 2014 Final Office Action dated Nov. 6, 2017.
U.S. Appl. No. 14/250,093, filed Apr. 10, 2014 Non-Final Office Action dated Nov. 16, 2016.
U.S. Appl. No. 14/250,093, filed Apr. 10, 2014 Panel Decision dated Jul. 14, 2017.
U.S. Appl. No. 14/250,093, filed Apr. 10, 2014 Patent Board Decision dated Jun. 8, 2020.
U.S. Appl. No. 14/477,717, filed Sep. 4, 2014, Notice of allowance dated Feb. 17, 2015.
U.S. Appl. No. 14/477,717, filed Sep. 4, 2014, Office action dated Dec. 18, 2014.
U.S. Appl. No. 14/585,800, filed Dec. 30, 2014 Final Office Action dated May 11, 2018.
U.S. Appl. No. 14/585,800, filed Dec. 30, 2014 Non-Final Office Action dated May 16, 2016.
U.S. Appl. No. 14/585,800, filed Dec. 30, 2014 Non-Final Office Action dated Nov. 29, 2016.
U.S. Appl. No. 14/585,800, filed Dec. 30, 2014 Non-Final Office Action dated Nov. 3, 2017.
U.S. Appl. No. 14/585,800, filed Dec. 30, 2014 Non-Final Office Action dated Oct. 8, 2015.
U.S. Appl. No. 14/585,800, filed Dec. 30, 2014 Notice of Allowance dated Feb. 25, 2019.
U.S. Appl. No. 14/585,800, filed Dec. 30, 2014 Notice of Allowance dated Jul. 3, 2017.
U.S. Appl. No. 14/702,580, filed May 1, 2015 Advisory Action dated Nov. 13, 2017.
U.S. Appl. No. 14/702,580, filed May 1, 2015 Final Office Action dated Sep. 1, 2017.

(56) References Cited

OTHER PUBLICATIONS

U.S. Appl. No. 14/702,580, filed May 1, 2015 Non-Final Office Action dated May 3, 2017.
U.S. Appl. No. 14/702,580, filed May 1, 2015 Notice of Allowance dated Dec. 8, 2017.
U.S. Appl. No. 14/750,658, filed Jun. 25, 2016 Non-Final Office Action dated Mar. 9, 2017.
U.S. Appl. No. 14/750,658, filed Jun. 25, 2016 Notice of Allowance dated Jul. 20, 2017.
U.S. Appl. No. 14/846,387, filed Sep. 4, 2015 Advisory Action dated May 10, 2018.
U.S. Appl. No. 14/846,387, filed Sep. 4, 2015 Final Office Action dated Mar. 22, 2018.
U.S. Appl. No. 14/846,387, filed Sep. 4, 2015 Non-Final Office Action dated Sep. 22, 2017.
U.S. Appl. No. 14/846,387, filed Sep. 4, 2015 Notice of Allowance dated Oct. 29, 2018.
U.S. Appl. No. 14/866,441, filed Sep. 25, 2015 Advisory Action dated Dec. 22, 2016.
U.S. Appl. No. 14/866,441, filed Sep. 25, 2015 Final Office Action dated Jun. 5, 2018.
U.S. Appl. No. 14/866,441, filed Sep. 25, 2015 Final Office Action dated Sep. 23, 2016.
U.S. Appl. No. 14/866,441, filed Sep. 25, 2015 Non-Final Office Action dated Apr. 7, 2017.
U.S. Appl. No. 14/866,441, filed Sep. 25, 2015 Non-Final Office Action dated Mar. 14, 2016.
U.S. Appl. No. 14/866,441, filed Sep. 25, 2015 Notice of Allowance dated Oct. 17, 2018.
U.S. Appl. No. 14/866,738, filed Sep. 25, 2015 Final Office Action dated Feb. 24, 2017.
U.S. Appl. No. 14/866,738, filed Sep. 25, 2015 Non-Final Office Action dated Nov. 6, 2017.
U.S. Appl. No. 14/866,738, filed Sep. 25, 2015 Non-Final Office Action dated Oct. 31, 2016.
U.S. Appl. No. 14/866,738, filed Sep. 25, 2015 Notice of Panel Decision dated Jun. 23, 2017.
U.S. Appl. No. 15/869,872, filed Jan. 12, 2018 Notice of Allowance dated Dec. 24, 2021.
U.S. Appl. No. 16/450,800, filed Jun. 24, 2019 Notice of Allowance dated Nov. 3, 2021.
U.S. Appl. No. 15/154,384, filed May 13, 2016 Final Office Action dated Dec. 24, 2020.
U.S. Appl. No. 15/154,384, filed May 13, 2016 Notice of Allowance dated Mar. 17, 2021.
U.S. Appl. No. 16/292,076, filed Mar. 4, 2019 Corrected Notice of Allowance dated Feb. 25, 2021.
U.S. Appl. No. 16/292,076, filed Mar. 4, 2019 Notice of Allowance dated Feb. 4, 2021.
U.S. Appl. No. 16/295,906, filed Mar. 7, 2019 Final Office Action dated Dec. 22, 2020.
U.S. Appl. No. 16/295,906, filed Mar. 7, 2019 Notice of Allowance dated Mar. 4, 2021.
U.S. Appl. No. 16/296,087, filed Mar. 7, 2019 Non-Final Office Action dated Mar. 26, 2021.
U.S. Appl. No. 16/296,087, filed Mar. 7, 2019 Restriction Requirement dated Feb. 8, 2021.
U.S. Appl. No. 16/389,719, filed Apr. 19, 2019 Non-Final Office Action dated Mar. 19, 2021.
U.S. Appl. No. 16/529,602, filed Aug. 1, 2019 Notice of Allowance dated Jan. 19, 2021.
U.S. Appl. No. 29/658,136, filed Jul. 27, 2018 Notice of Allowance dated Mar. 23, 2021.
Access Scientific, The PICC Wand® Product Data Sheet, Revision F, May 22, 2012.
Access Scientific, The Powerwand® Extended Dwell Catheter Brochure (http://accessscientific.com/media/4Fr-POWERWAND-Brochure.pdf) last accessed Sep. 25, 2015.
BD Angiocath™ Autoguard™ Shielded IV Catheter Brochure, © 2001.
BD Medical Systems, I.V. Catheter Family Brochure (2006).
BD Saf-T-Intima™ Integrated Safety IV Catheter Brochure, © 2001.
Becton Dickinson, Insyte® AutoGuard™ Shielded I.V. Catheter Brochure, 1998.
CA 2,799,360 filed May 13, 2011 Office Action dated Jun. 7, 2017.
CN 201180029526.7 filed Dec. 14, 2012 First Office Action dated Apr. 21, 2014.
CN 2012800008866.6 filed Aug. 14, 2013 Second Office Action dated Aug. 17, 2015.
CN 201280008866.6 filed Aug. 14, 2013 First Office Action dated Dec. 31, 2014.
CN 201280008866.6 filed Aug. 14, 2013 Third Office Action dated Jan. 25, 2016.
CN 201380073657.4 filed Aug. 21, 2015 Office Action dated Jun. 28, 2017.
CN 201380073657.4 filed Aug. 21, 2015 Office Action dated Mar. 2, 2018.
CN 201480019467.9 filed Sep. 29, 2015 Office Action dated Apr. 6, 2017.
CN 201510079782.7 filed Feb. 13, 2015 Office Action dated Dec. 30, 2016.
CN 201510079782.7 filed Feb. 13, 2015 Office Action dated Feb. 5, 2018.
CN 201510079782.7 filed Feb. 13, 2015 Office Action dated Sep. 19, 2017.
CN 201580022407.7 filed Nov. 2, 2016 Office Action dated Jan. 31, 2019.
CN 201580022407.7 filed Nov. 2, 2016 Office Action dated Sep. 16, 2019.
Cook Medical "Lunderquist Extra-Stiff wire guide" (2012).
Endovascular Today "Coiled Stainless Steel Guidewires" Buyer's Guide pp. 13-20, (2012).
EP 07783404.2 filed Jan. 19, 2009 Office Action dated Apr. 16, 2019.
EP 07783404.2 filed Jan. 19, 2009 Office Action dated Mar. 7, 2018.
EP 10075422.5 filed Jul. 5, 2008 European search report and written opinion dated Dec. 1, 2010.
EP 11781384.0 filed Sep. 21, 2012 Extended European Search Report dated Oct. 31, 2017.
EP 12782187.4 filed Sep. 10, 2013 European search report and written opinion dated Aug. 30, 2016.
EP 12782187.4 filed Sep. 10, 2013 European search report and written opinion dated Dec. 17, 2015.
EP 12782187.4 filed Sep. 10, 2013 Office Action dated Apr. 24, 2018.
EP 12782187.4 filed Sep. 10, 2013 Office Action dated Nov. 28, 2018.
EP 13876666.2 filed Sep. 7, 2015 Extended European Search Report dated Sep. 20, 2016.
EP 15785819.2 filed Dec. 2, 2016 Extended European Search Report dated Dec. 4, 2017.
EP 16797029.2 filed Nov. 21, 2017 Extended European Search Report dated May 3, 2018.
EP 16797029.2 filed Nov. 21, 2017 Office Action dated Mar. 27, 2020.
EP 16797047.4 filed Dec. 6, 2017 Supplemental European Search Report dated Jan. 9, 2019.
EP 19181963.0 filed Jun. 24, 2019 Extended European Search Report dated Jul. 16, 2019.
EP17849786.3 filed Apr. 12, 2019 Extended European Search Report dated May 13, 2020.
European office action dated Apr. 21, 2008 for EP Application No. 06800027.2.
European office action dated Aug. 6, 2012 for EP Application No. 07783404.2.
European office action dated Oct. 5, 2010 for EP Application No. 07783404.2.
European search report and opinion dated Jul. 10, 2009 for EP Application No. 07783404.2.
Hadaway, Lynn C., A Midline Alternative to Central and Peripheral Venous Access, Caring Magazine, May 1990, pp. 45-50.

(56) References Cited

OTHER PUBLICATIONS

International search report and written opinion dated Apr. 2, 2012 for PCT/US2012/023192.
International search report and written opinion dated Jun. 1, 2007 for PCT/US2006/026671.
International search report and written opinion dated Oct. 23, 2008 for PCT/US2007/068393.
JP 2013-510353 filed Oct. 31, 2012 First Office Action dated Feb. 19, 2015.
JP 2013-510353 filed Oct. 31, 2012 Office Action dated Dec. 15, 2016.
JP 2013-510353 filed Oct. 31, 2012 Second Office Action dated Jan. 28, 2016.
JP 2015-560173 filed Aug. 28, 2015 Office Action dated Aug. 2, 2018.
JP 2015-560173 filed Aug. 28, 2015 Office Action dated Sep. 19, 2017.
JP 2016-107046 filed May 30, 2016 Office Action dated Apr. 26, 2017.
PCT/US2019/021231 filed Mar. 7, 2019 International Search Report and Written Opinion, dated Jun. 27, 2019.
U.S. Appl. No. 14/250,093, filed Apr. 10, 2014 Notice of Allowance dated Aug. 19, 2020.
U.S. Appl. No. 14/866,738, filed Sep. 25, 2015 Notice of Allowance dated Sep. 24, 2020.
U.S. Appl. No. 15/862,380, filed Jan. 4, 2018 Final Office Action dated Oct. 26, 2020.
U.S. Appl. No. 15/869,872, filed Jan. 12, 2018 Advisory Action dated Sep. 23, 2020.
U.S. Appl. No. 16/292,076, filed Mar. 4, 2019 Non-Final Office Action dated Aug. 10, 2020.
U.S. Appl. No. 16/295,906, filed Mar. 7, 2019 Non-Final Office Action dated Sep. 4, 2020.
U.S. Appl. No. 29/654,521, filed Jun. 25, 2018 Notice of Allowability dated Sep. 30, 2020.
U.S. Appl. No. 29/654,521, filed Jun. 25, 2018 Notice of Allowance dated Aug. 17, 2020.
U.S. Appl. No. 29/654,527, filed Jun. 25, 2018 Notice of Allowability dated Sep. 30, 2020.
U.S. Appl. No. 29/654,527, filed Jun. 25, 2018 Notice of Allowance dated Aug. 18, 2020.
U.S. Appl. No. 29/658,136, filed Jul. 27, 2018 Non-Final Office Action dated Sep. 9, 2020.
U.S. Appl. No. 14/866,738, filed Sep. 25, 2015 Patent Board Decision—Examiner Affirmed in Part dated Jul. 13, 2020.
U.S. Appl. No. 14/876,735, filed Oct. 6, 2015 Non-Final Office Action dated Mar. 30, 2017.
U.S. Appl. No. 15/154,384, filed May 13, 2016 Final Office Action dated Nov. 27, 2019.
U.S. Appl. No. 15/154,384, filed May 13, 2016 Non-Final Office Action dated Jun. 26, 2020.
U.S. Appl. No. 15/154,384, filed May 13, 2016 Non-Final Office Action dated Jun. 28, 2019.
U.S. Appl. No. 15/154,384, filed May 13, 2016 Restriction Requirment dated Jan. 25, 2019.
U.S. Appl. No. 15/154,808, filed May 13, 2016 Advisory Action dated Oct. 26, 2018.
U.S. Appl. No. 15/154,808, filed May 13, 2016 Final Office Action dated Aug. 16, 2018.
U.S. Appl. No. 15/154,808, filed May 13, 2016 Non-Final Office Action dated Apr. 6, 2018.
U.S. Appl. No. 15/154,808, filed May 13, 2016 Notice of Allowance dated Apr. 16, 2019.
U.S. Appl. No. 15/154,808, filed May 13, 2016 Restriction Requirement dated Jan. 3, 2018.
U.S. Appl. No. 15/377,880, filed Dec. 13, 2016 Final Office Action dated Oct. 19, 2018.
U.S. Appl. No. 15/377,880, filed Dec. 13, 2016 Non-Final Office Action dated May 14, 2018.
U.S. Appl. No. 15/481,773, filed Apr. 7, 2017 Final Office Action dated Jan. 10, 2019.
U.S. Appl. No. 15/481,773, filed Apr. 7, 2017 Non-Final Office Action dated Jun. 29, 2018.
U.S. Appl. No. 15/608,802, filed May 30, 2017 Non-Final Office Action dated Jun. 6, 2019.
U.S. Appl. No. 15/692,915, filed Aug. 31, 2017 Non-Final Office Action dated Jan. 29, 2018.
U.S. Appl. No. 15/702,537, filed Sep. 12, 2017 Final Office Action dated Mar. 8, 2019.
U.S. Appl. No. 15/702,537, filed Sep. 12, 2017 Non-Final Office Action dated Nov. 29, 2018.
U.S. Appl. No. 15/702,537, filed Sep. 12, 2017 Notice of Allowance dated Jul. 31, 2019.
U.S. Appl. No. 15/727,528, filed Oct. 6, 2017 Final Office Action dated Jan. 28, 2020.
U.S. Appl. No. 15/727,528, filed Oct. 6, 2017 Non-Final Office Action dated Sep. 20, 2019.
U.S. Appl. No. 15/727,528, filed Oct. 6, 2017 Restriction Requirement dated Aug. 7, 2019.
U.S. Appl. No. 15/727,528, filed Oct. 6, 2017 Notice of Allowance dated Mar. 27, 2020.
U.S. Appl. No. 15/862,380, filed Jan. 4, 2018 Non-Final Office Action dated Jul. 9, 2020.
U.S. Appl. No. 15/862,380, filed Jan. 4, 2018 Restriction Requirement dated Dec. 23, 2019.
U.S. Appl. No. 15/869,872, filed Jan. 12, 2018 Final Office Action dated Jun. 25, 2020.
U.S. Appl. No. 15/869,872, filed Jan. 12, 2018 Non-Final Office Action dated Apr. 10, 2020.
U.S. Appl. No. 15/951,931, filed Apr. 12, 2018 Non-Final Office Action dated Nov. 19, 2019.
U.S. Appl. No. 15/951,931, filed Apr. 12, 2018 Notice of Allowance dated Feb. 20, 2020.
U.S. Appl. No. 15/951,931, filed Apr. 12, 2018 Notice of Allowability dated Apr. 16, 2020.
U.S. Appl. No. 15/951,954, filed Apr. 12, 2018 Non-Final Office Action dated Nov. 4, 2019.
U.S. Appl. No. 15/951,954, filed Apr. 12, 2018 Notice of Allowance dated Feb. 23, 2020.
U.S. Appl. No. 15/951,954, filed Apr. 12, 2018 Notice of Allowability dated Apr. 7, 2020.
U.S. Appl. No. 16/138,523, filed Sep. 21, 2018 Notice of Allowance dated Mar. 26, 2020.
U.S. Appl. No. 29/536,043, filed Aug. 12, 2015 Final Office Action dated Mar. 26, 2018.
U.S. Appl. No. 29/536,043, filed Aug. 12, 2015 Non-Final Office Action dated Aug. 31, 2017.
U.S. Appl. No. 29/545,436, filed Nov. 12, 2015 Final Office Action dated Mar. 26, 2018.
U.S. Appl. No. 29/545,436, filed Nov. 12, 2015 Non-Final Office Action dated Sep. 12, 2017.
U.S. Appl. No. 29/654,521, filed Jun. 25, 2018 Restriction Requirement dated Apr. 8, 2020.
U.S. Appl. No. 29/654,527, filed Jun. 25, 2018 Restriction Requirement dated Mar. 10, 2020.
U.S. Appl. No. 29/658,136, filed Jul. 27, 2018 Restriction Requirement dated May 11, 2020.
Waltimire, B. and Rasor, J.S., Midline catheter: Virtually bloodless insertion technique and needle safety tube minimize potential for transmission of bloodborne disease. Sponsored by national Foundation for Infectious Diseases. 5th National forum on AIDS, Hepatitis, and other blood-borne diseases. Atlanta, GA, Mar. 1992.
JP 2016-107046 filed May 30, 2016 Office Action dated Jul. 28, 2016.
JP 2016-107046 filed May 30, 2016 Office Action dated Nov. 7, 2017.
JP 2016-563441 filed Oct. 19, 2016 Office Action dated Jan. 25, 2019.
JP 2018-039302 filed Mar. 6, 2018 Office Action dated Feb. 20, 2019.
Menlo Care, Landmark™ Aquavene® Catheters Brochure, 1992.

(56) References Cited

OTHER PUBLICATIONS

Menlo Care, Landmark® Midline Catheter Maintenance and Reference Guide (1993).
Menlo Care, Landmark® Midline Catheters Brochure, 1991.
Menlo Care, Landmark® Venous Access Device Insertion Instructions (1992).
Menlo Care, Publications on Aquavene® Technology, Aug. 1992.
Notice of allowance dated Jan. 29, 2014 for U.S. Appl. No. 12/307,519.
Notice of allowance dated Jun. 10, 2015 for U.S. Appl. No. 11/577,491.
Office action dated Mar. 10, 2011 for U.S. Appl. No. 12/307,519.
Office action dated Mar. 15, 2011 for U.S. Appl. No. 11/577,491.
Office action dated Mar. 27, 2013 for U.S. Appl. No. 13/358,099.
Office action dated Aug. 2, 2010 for U.S. Appl. No. 11/577,491.
Office action dated Aug. 18, 2014 for U.S. Appl. No. 11/577,491.
Office action dated Oct. 25, 2010 for U.S. Appl. No. 12/307,519.
Office action dated Nov. 4, 2013 for U.S. Appl. No. 12/307,519.
Office action dated Mar. 12, 2015 for U.S. Appl. No. 11/577,491.
PCT/CN2017/075370 filed Mar. 1, 2017 International Search Report and Written Opinion dated Nov. 30, 2017.
PCT/US15/28950 filed May 1, 2015 International Search Report and Written Opinion dated Oct. 19, 2015.
PCT/US2008/062954 filed May 7, 2008 International search report and written opinion dated Jan. 16, 2009.
PCT/US2011/036530 filed May 13, 2011 International Search Report dated Oct. 6, 2011.
PCT/US2011/036530 filed May 13, 2011 Written Opinion of the International Searching Authority dated Oct. 6, 2011.
PCT/US2012/026618 International Preliminary Report on Patentability dated Aug. 27, 2013.
PCT/US2012/026618 International Search Report and Written Opinion dated Jun. 25, 2012.
PCT/US2013/073577 filed Dec. 6, 2013 International Search Report and Written Opinion dated Feb. 24, 2014.
PCT/US2014/013557 filed Jan. 29, 2014 International search report and written opinion dated Apr. 14, 2014.
PCT/US2015/048676 filed Sep. 4, 2015 International search report and written opinion dated Dec. 4, 2015.
PCT/US2016/032449 filed May 13, 2016 International Search Report and Written Opinion dated Oct. 5, 2016.
PCT/US2016/032534 filed May 13, 2016 International Search Report and Written Opinion dated Oct. 5, 2016.
PCT/US2017/051214 filed Sep. 12, 2017 International Search Report and Written Opinion dated Nov. 13, 2017.
PR Newswire, Luther Medical Products, Inc. Receives Approval to Supply Improved Neonatal Product to Japan, Aug. 20, 1998.
Rasor, Julia S, Review of Catheter-related infection rates: comparison of conventional catheter materials with Aquavene®, JVAN vol. 1, No. 3, Spring 1991.
RU 2017141812 filed Nov. 30, 2017 Office Action dated Jan. 31, 2018.
SG 11201709185X filed Nov. 8, 2017 Office Action dated Oct. 5, 2018.
SG 11201709193S filed Nov. 8, 2017 Office Action dated Oct. 5, 2018.
U.S. Appl. No. 12/598,053, filed Apr. 20, 2010 Notice of allowance dated Jan. 16, 2014.
U.S. Appl. No. 12/598,053, filed Apr. 20, 2010 Office action dated Aug. 28, 2013.
U.S. Appl. No. 12/598,053, filed Apr. 20, 2010 Office action dated Dec. 4, 2012.
U.S. Appl. No. 12/598,053, filed Apr. 20, 2010 Office action dated May 8, 2013.
U.S. Appl. No. 12/598,053, filed Apr. 20, 2010 Office action dated Oct. 24, 2013.
U.S. Appl. No. 13/107,781, filed May 13, 2011 Final Office Action dated Jul. 18, 2014.
U.S. Appl. No. 13/107,781, filed May 13, 2011 Non-Final Office Action dated Dec. 30, 2013.
U.S. Appl. No. 13/405,096, filed Feb. 24, 2012 Advisory Action dated Apr. 18, 2014.
U.S. Appl. No. 13/405,096, filed Feb. 24, 2012 Final Office Action dated Jan. 31, 2014.
U.S. Appl. No. 13/405,096, filed Feb. 24, 2012 Non-Final Office Action dated Aug. 20, 2013.
U.S. Appl. No. 13/405,096, filed Feb. 24, 2012 Non-Final Office Action dated Nov. 18, 2014.
U.S. Appl. No. 13/405,096, filed Feb. 24, 2012 Notice of Allowance dated Mar. 11, 2015.
U.S. Appl. No. 14/044,623, filed Oct. 2, 2013 Notice of Allowance dated Nov. 6, 2014.
U.S. Appl. No. 15/154,384, filed May 13, 2016 Notice of Allowance dated Apr. 29, 2021.
U.S. Appl. No. 15/862,380, filed Jan. 4, 2018 Notice of Allowance dated Jun. 16, 2021.
U.S. Appl. No. 16/296,087, filed Mar. 7, 2019 Final Office Action dated Sep. 10, 2021.
U.S. Appl. No. 16/389,719, filed Apr. 19, 2019 Final Office Action dated Jun. 14, 2021.
U.S. Appl. No. 16/450,800, filed Jun. 24, 2019 Non-Final Office Action dated Jul. 9, 2021.
U.S. Appl. No. 16/490,023, filed Aug. 29, 2019 Non-Final Office Action dated Oct. 4, 2021.
U.S. Appl. No. 16/490,023, filed Aug. 29, 2019 Restriction Requirement dated May 4, 2021.
U.S. Appl. No. 16/529,622, filed Aug. 1, 2019 Non-Final Office Action dated May 7, 2021.
U.S. Appl. No. 16/529,622, filed Aug. 1, 2019 Notice of Allowance dated Aug. 23, 2021.
U.S. Appl. No. 17/164,653, filed Feb. 1, 2021, Notice of Allowance dated Nov. 1, 2022.
U.S. Appl. No. 17/337,273, filed Jun. 2, 2021 Notice of Allowance dated Oct. 5, 2022.
EP 22159383.3 filed Mar. 1, 2022 Extended European Search Report dated May 30, 2022.
PCT/US2019/052225 filed Sep. 20, 2019 International Search Report and Written Opinion dated Jun. 25, 2020.
PCT/US2020/046860 filed Aug. 18, 2020 International Search Report and Written Opinion dated Nov. 18, 2020.
U.S. Appl. No. 16/296,087, filed Mar. 7, 2019 Notice of Allowance dated Mar. 8, 2022.
U.S. Appl. No. 16/490,023, filed Aug. 29, 2019 Notice of Allowance dated Mar. 14, 2022.
U.S. Appl. No. 16/696,844, filed Nov. 26, 2019 Non-Final Office Action dated Aug. 1, 2022.
U.S. Appl. No. 16/868,461, filed May 6, 2020 Final Office Action dated May 25, 2022.
U.S. Appl. No. 16/868,461, filed May 6, 2020 Non-Final Office Action dated Feb. 15, 2022.
U.S. Appl. No. 16/996,769, filed Aug. 18, 2020 Non-Final Office Action dated Mar. 2, 2022.
U.S. Appl. No. 16/996,769, filed Aug. 18, 2020 Notice of Allowance dated Jun. 13, 2022.
U.S. Appl. No. 17/164,653, filed Feb. 1, 2021, Restriction Requirement dated Sep. 7, 2022.
EP 22192364.2 filed Aug. 26, 2022 Extended European Search Report dated Nov. 30, 2022.
U.S. Appl. No. 16/868,461, filed May 6, 2020 Examiner's Answer dated Jan. 31, 2023.
U.S. Appl. No. 16/902,031, filed Jun. 15, 2020 Non-Final Office Action dated Dec. 21, 2022.
U.S. Appl. No. 17/471,051, filed Sep. 9, 2021 Restriction Requirement dated Dec. 22, 2022.
U.S. Appl. No. 17/863,179, filed Jul. 12, 2022 Non-Final Office Action dated Dec. 7, 2022.
U.S. Appl. No. 16/696,844, filed Nov. 26, 2019 Notice of Allowance dated Apr. 17, 2023.
U.S. Appl. No. 17/353,602, filed Jun. 21, 2021 Non-Final Office Action dated Mar. 30, 2023.
U.S. Appl. No. 17/471,051, filed Sep. 9, 2021 Non-Final Office Action dated May 24, 2023.

(56) References Cited

OTHER PUBLICATIONS

U.S. Appl. No. 18/094,917, filed Jan. 9, 2023 Non-Final Office Action dated Jun. 8, 2023.
EP 20855351.1 filed Mar. 7, 2022 Extended European Search Report dated Sep. 7, 2023.
U.S. Appl. No. 16/902,031, filed Jun. 15, 2020 Final Office Action dated Aug. 18, 2023.
U.S. Appl. No. 17/471,051, filed Sep. 9, 2021 Final Office Action dated Aug. 23, 2023.
U.S. Appl. No. 17/493,806, filed Oct. 4, 2021 Non-Final Office Action dated Jul. 31, 2023.
U.S. Appl. No. 17/863,179, filed Jul. 12, 2022 Advisory Action dated Aug. 23, 2023.
U.S. Appl. No. 18/094,917, filed Jan. 9, 2023 Notice of Allowance dated Sep. 13, 2023.

\* cited by examiner

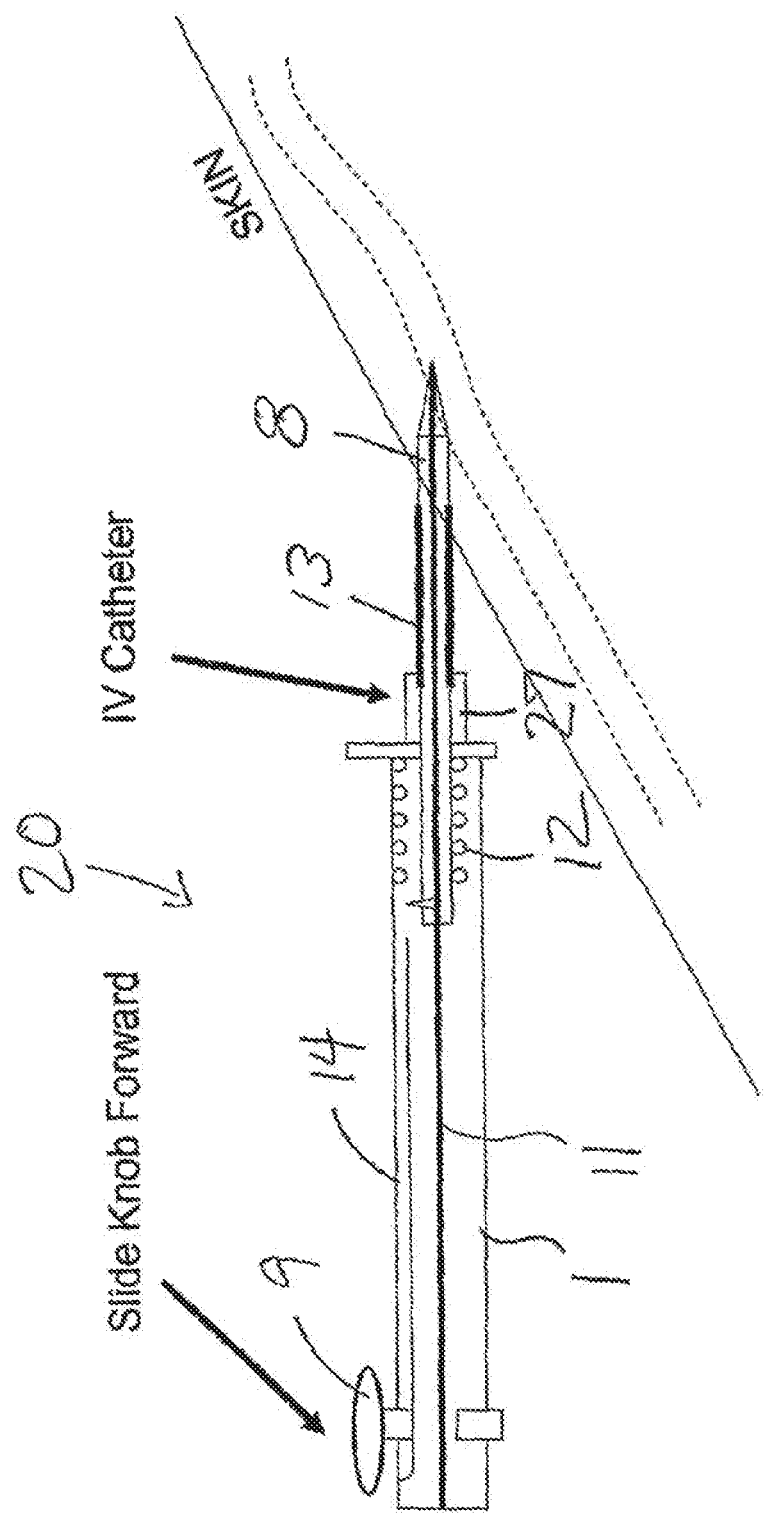

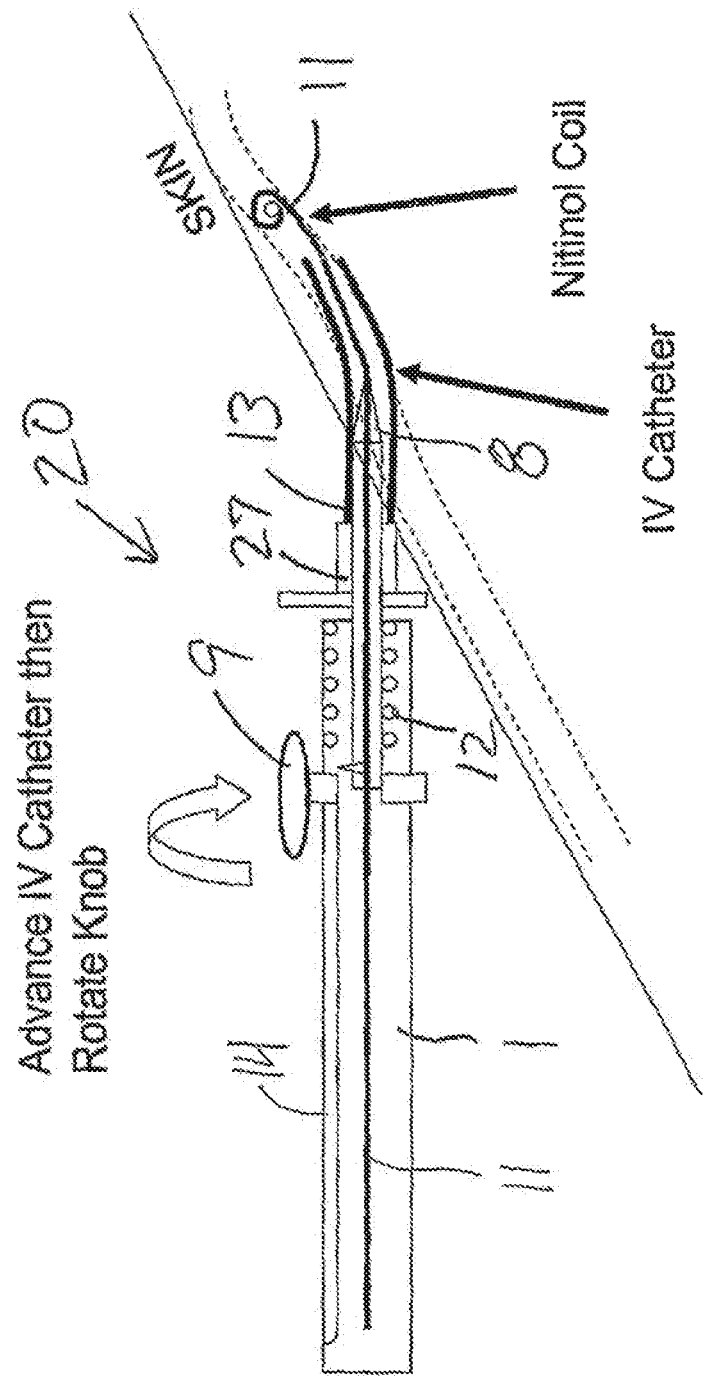

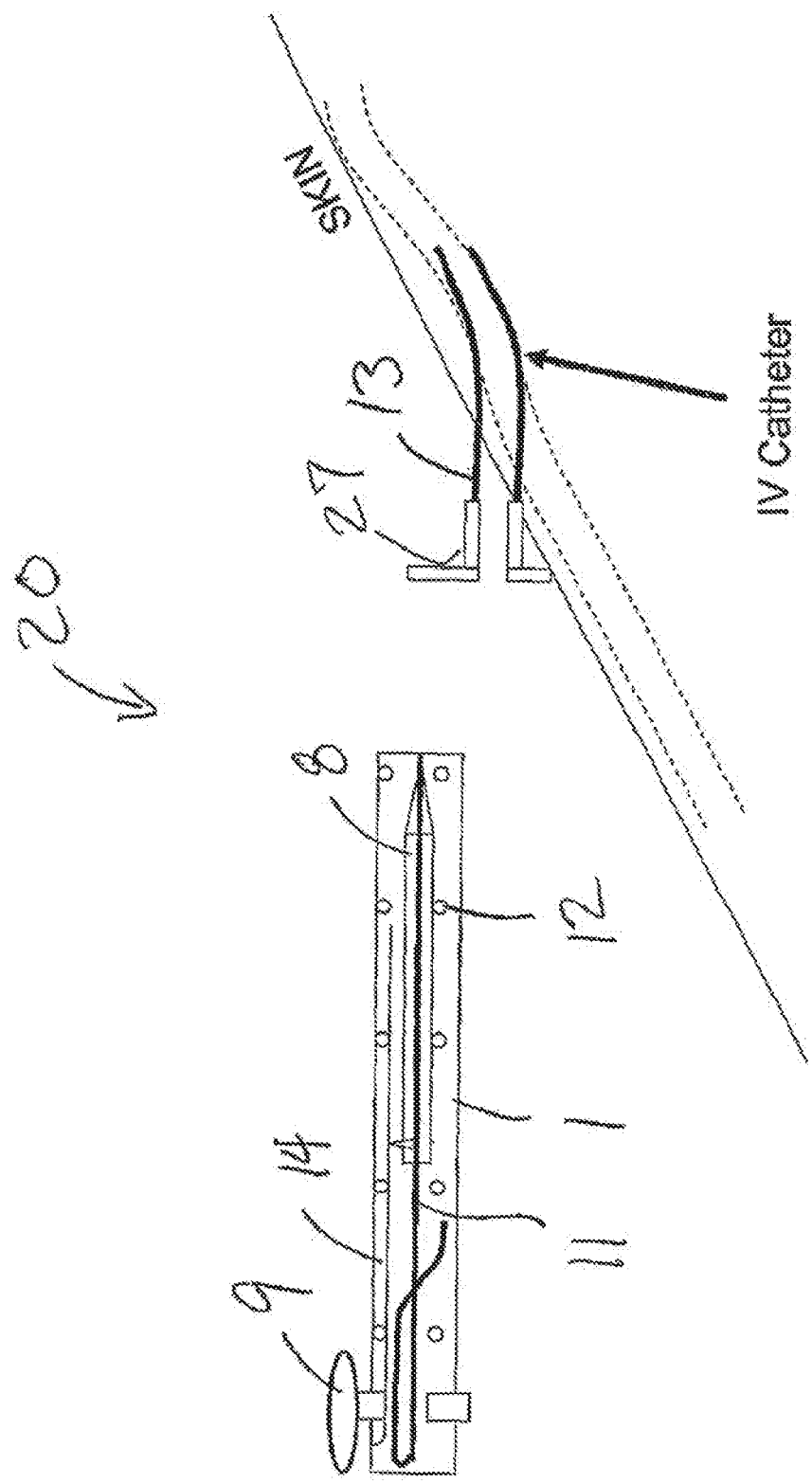

INTRAVENOUS CATHETER INSERTION DEVICE

CROSS REFERENCE TO RELATED APPLICATIONS

This application is a continuation of U.S. patent application Ser. No. 16/292,076, filed Mar. 4, 2019, now U.S. Pat. No. 10,220,191, which is a continuation of U.S. patent application Ser. No. 14/866,441, filed Sep. 25, 2015, now U.S. Pat. No. 10,220,191, which is a continuation of U.S. patent application Ser. No. 11/577,491, filed Aug. 20, 2008, now U.S. Pat. No. 9,162,037, which is a U.S. national stage application under 35 U.S.C. § 371 of International Application No. PCT/US2006/026671, filed Jul. 6, 2006, which claims the benefit of priority to U.S. Provisional Application No. 60/697,333, filed Jul. 6, 2005, each of which is incorporated by reference in its entirety into this application.

FIELD OF THE INVENTION

The present invention relates to devices and methods for insertion and placement of an intravenous catheter into a vein or artery of a patient. The devices and methods of the invention facilitate safe placement of the catheter into the patient's vein or artery, which is of particular importance in the case of small, tortuous, collapsed, fragile, and/or difficult to locate vessels. The devices and methods also provide protection against accidental punctures and/or contamination by the needle after placement of the intravenous catheter.

BACKGROUND OF THE INVENTION

The following patents and publications describe prior intravenous catheter insertion devices and/or safety devices for syringes and needles: EP Patent No. 0 515 710 B1 to Haining, titled, "Intravenous catheter and insertion device"; U.S. Pat. No. 5,019,049 to Haining, titled, "Intravenous catheter and insertion device"; U.S. Pat. No. 5,176,650 to Haining, titled, "Intravenous catheter and insertion device"; EP Patent No. 0 567 321 B1 to Chang, titled, "Intravenous catheter with needle guard"; EP Patent No. 0 652 020 B1 to Mahurkar, titled, "Retractable hypodermic needle assembly"; EP Patent No. 0 910 988 B1 to Mahurkar, titled, "Blood sample collection assembly"; U.S. Pat. No. 5,891,105 to Mahurkar, titled, "Hypodermic needle assembly"; U.S. Pat.t No. 3,572,334 to DeWitt, titled, "Intravenous catheter placement unit"; EP Publication No. 0 750 916 to van Heugten, titled, "Protective needle cover containment"; EP Patent No. 0 942 761 B1 to Botich, titled, "Medical device with retractable needle"; EP Patent No. 1 075 850 B1 to Botich, titled, "Apparatus for intravenous catheter insertion"; U.S. Pat. No. 5,800,395 to Botich et al, titled, "Medical device with retractable needle"; U.S. Pat. No. 6,436,070 to Botich et al, titled, "Catheter insertion device with retractable needle"; U.S. Patent Publication No. 2003/060760 to Botich et al, titled, "Catheter insertion device with retractable needle"; WO 2000/012160 to Botich et al, titled, "Fluid infusion device with retractable needle"; WO 1996/032981 to Botich et al, titled, "Safety stylet for intravenous catheter insertion"; WO 1998/024494 to Botich et al, titled, "Medical device with retractable needle"; EP Patent No. 1 457 229 B1 to Shue, titled, "Intravenous catheter inserting device"; U.S. Patent Publication No. 2004/106903 to Shue, titled, "Intravenous catheter inserting device"; U.S. Pat. No. 3,592,192 to Harautuneian, titled, "Intravenous catheter apparatus with catheter telescoped on outside of puncturing cannula"; U.S. Pat. No. 3,610,240 to Harautuneian, titled, "Intravenous catheter apparatus with catheter telescoped inside puncturing cannula"; U.S. Pat. No. 4,037,600 to Poncy et al, titled, "Catheter placement system"; U.S. Pat. No. 4,292,970 to Hession, titled, "Apparatus for intravenous catheter starter"; U.S. Pat. No. 4,834,718 to McDonald, titled, "Safety needle apparatus"; U.S. Pat. No. 4,944,725 to McDonald, titled, "Safety needle apparatus"; U.S. Pat. No. 4,909,793 to Vining et al, titled, "Intravenous catheter apparatus with retractable stylet"; U.S. Patent No. 4,944,728 to Carrell et al, titled, "Intravenous catheter placement device"; U.S. Pat. No. 4,966,589 to Kaufman, titled, "Intravenous catheter placement device"; U.S. Pat. No. 5,007,901 to Shields, titled, "Intravenous catheter insertion device"; U.S. Pat. No. 5,562,629 to Haughton et al, titled, "Catheter placement system utilizing a handle, a sharp, and a releasable retainer mechanism providing retraction of the sharp upon disengagement of the catheter from the handle"; U.S. Pat. No. 5,562,634 to Flumene et al, titled, "Intravenous catheter with automatically retracting needle-guide"; U.S. Pat. No. 5,573,510 to Isaacson titled, "Safety intravenous catheter assembly with automatically retractable needle"; U.S. Pat. No. 6,056,726 to Isaacson, titled, "Self-contained safety intravenous catheter insertion device"; WO 1995/023003 to Isaacson, titled, "Self-contained safety intravenous catheter insertion device"; U.S. Pat. No. 5,891,098 to Huang, titled, "Safety intravenous catheter"; U.S. Pat. No. 5,941,854 to Bhitiyakul, titled, "Intravenous catheter"; U.S. Pat. No. 5,997,507 to Dysarz titled, "Biased spring hard needle retractable IV catheter"; U.S. Pat. No. 6,193,690 to Dysarz titled, "Inclined plane latching device for an IV catheter"; U.S. Pat. No. 6,221,047 to Greene et al, titled, "Safety intravenous catheter assembly and method for use with a needle"; U.S. Pat. No. 6,689,102 to Greene et al, titled, "Safety intravenous catheter assembly"; U.S. Pat. No. 6,695,814 to Greene et al, titled, "Safety intravenous catheter assembly and method for use with a needle"; U.S. Patent Publication No. 2001/014786 to Greene et al, titled, "Safety intravenous catheter assembly and method for use with a needle"; U.S. Patent Publication No. 2002/165497 to Greene et al, titled, "Safety intravenous catheter assembly"; WO 2000/006226 to Greene et al, titled, "Safety intravenous catheter assembly and method for use with a needle"; U.S. Pat. No. 6,322,537 to Chang, titled, "Safety intravenous catheter"; U.S. Pat. No. 6,620,136 to Pressly, Sr. et al, titled, "Retractable IV catheter placement device"; WO 2000/047256 to Pressly, Sr. et al, titled, "Retractable IV catheter placement device"; U.S. Pat. No. 6,730,062 to Hoffman et al, titled, "Safety catheter with non-removable retractable needle"; U.S. Patent Publication No. 2003/073956 to Hoffman et al, titled, "Safety catheter with non-removable retractable needle"; U.S. Patent Publication No. 2004/267204 to Brustowicz, titled, "On-demand needle retaining and locking mechanism for use in intravenous catheter assemblies"; WO 2003/043686 to Garcia Andreo, titled, "Flow regulating/autovalve intravenous catheter"; WO 1992/022344 to Sircom, titled, "Needle guard for intravenous catheter placement"; WO 1995/019193 to Ogle, titled, "Retractable venipuncture catheter needle and receptacle"; WO 1997/005912 to Rohrbough et al, titled, "Retractable venipuncture catheter needle and receptacle"; and WO 1997/021458 to Hwang, titled, "Intravenous catheter with flexible extender and protector against needle tip."

SUMMARY OF THE INVENTION

In one aspect, the present invention takes the form of an intravenous catheter insertion device that provides coordinated movement of an access needle, an intravenous catheter and a safety guidewire. The device holds the access needle and the intravenous catheter in a coaxial arrangement for puncturing a vein or other target vessel. A blood flashback chamber provides a visual indication that the tip of the needle is in the lumen of the vein. Upon vein puncture by the access needle, a flexible safety guidewire is advanced through the access needle into the lumen of the vein using an actuation member located on the exterior of the device. With the flexible safety guidewire deployed within the lumen of the vein, the access needle and the intravenous catheter can be safely advanced into the vein until the tip of the intravenous catheter is also within the lumen of the vein. Alternatively, the intravenous catheter can be advanced separately while holding the access needle stationary. Then, the actuation member is actuated to simultaneously withdraw the access needle and the safety guidewire. Preferably, the access needle and the safety guidewire are withdrawn automatically by the action of a spring or other biasing member, leaving only the intravenous catheter in the vein. Once the access needle and the safety guidewire have been withdrawn, the intravenous catheter can be disconnected from the insertion device and connected to a source of intravenous fluid, medication, etc.

In another aspect, the present invention provides an improved method for insertion and placement of an intravenous catheter. The method includes the steps of: puncturing a vein or other target vessel with an access needle arranged coaxially with an intravenous catheter; verifying the location of the access needle tip in the lumen of the vein; advancing a safety guidewire through the access needle into the lumen of the vein, advancing the tip of the intravenous catheter into the vein; and simultaneously withdrawing the access needle and the safety guidewire from the intravenous catheter and from the patient.

Although the invention is described in relation to insertion of an intravenous catheter, the apparatus and methods described herein could readily be adapted for insertion of any catheter or similar device into a vein, artery or other internal body structure.

BRIEF DESCRIPTION OF THE DRAWINGS

FIGS. 7-9 illustrate a method of intravenous catheter insertion according to the present invention.

DETAILED DESCRIPTION OF THE INVENTION

Figure 1:
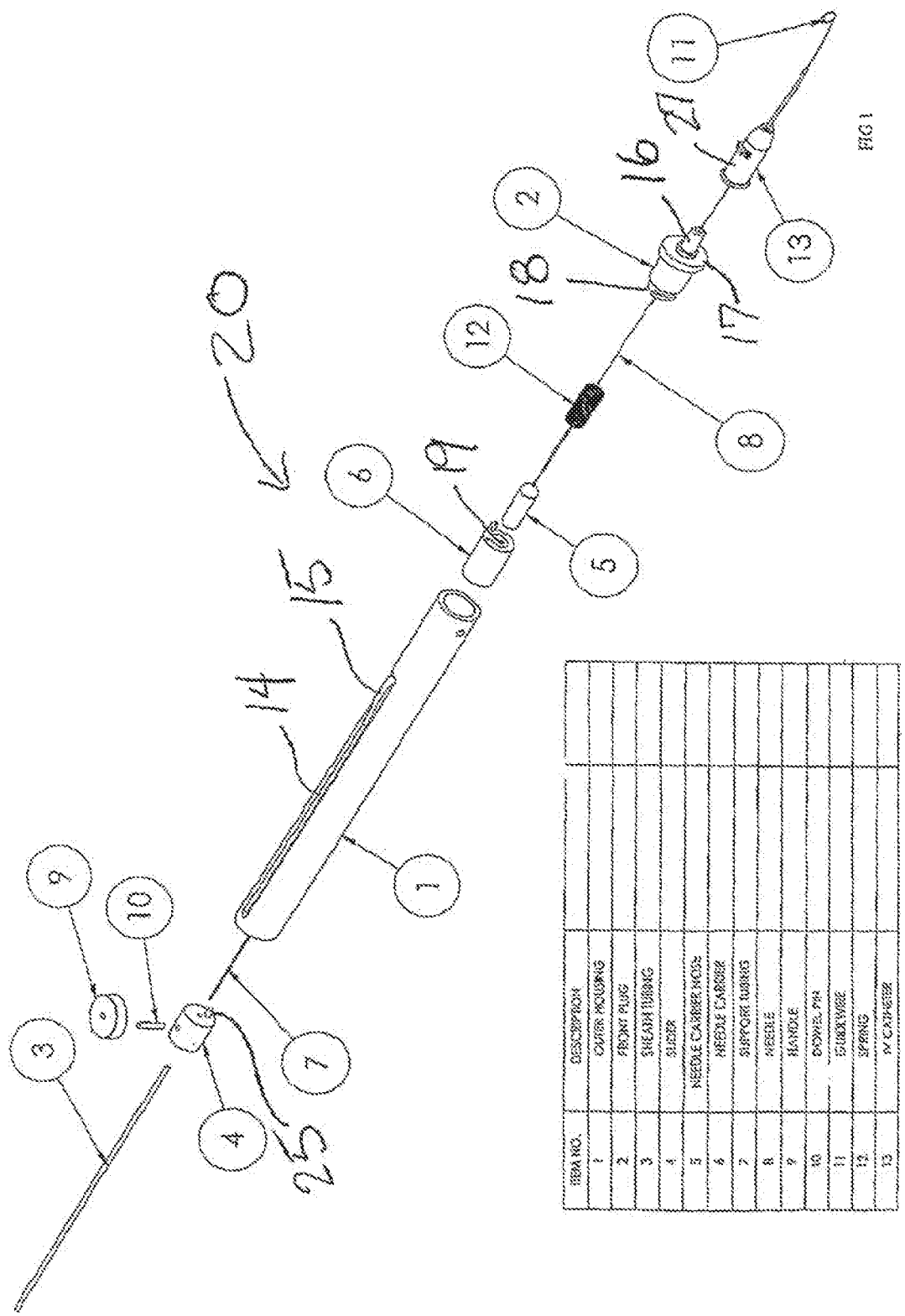
FIG. 1 shows an exploded view of an intravenous catheter insertion device according to the present invention.
Figure 2:
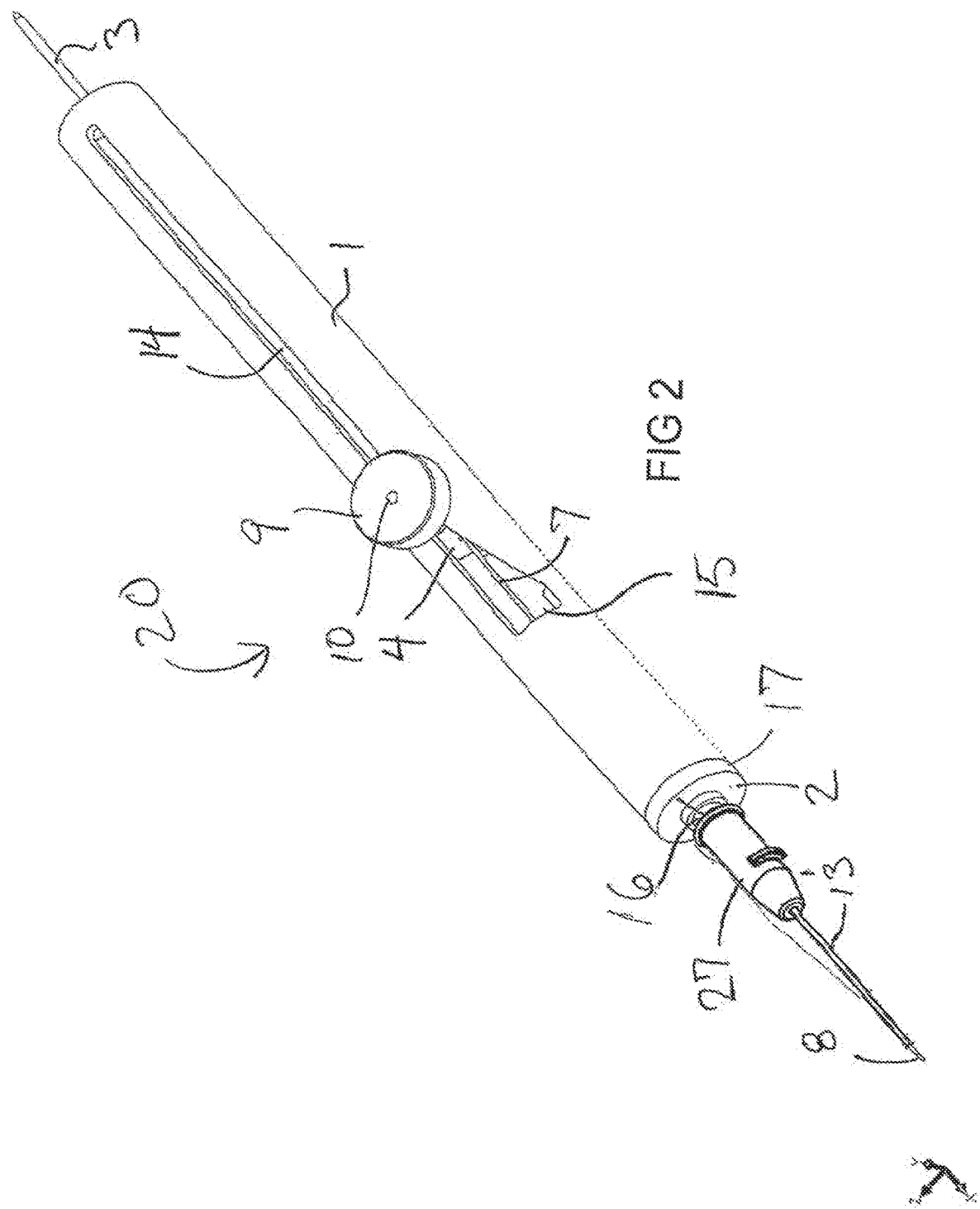
FIG. 2 shows an assembly drawing of the intravenous catheter insertion device in an undeployed state, ready for use.
Figure 3:
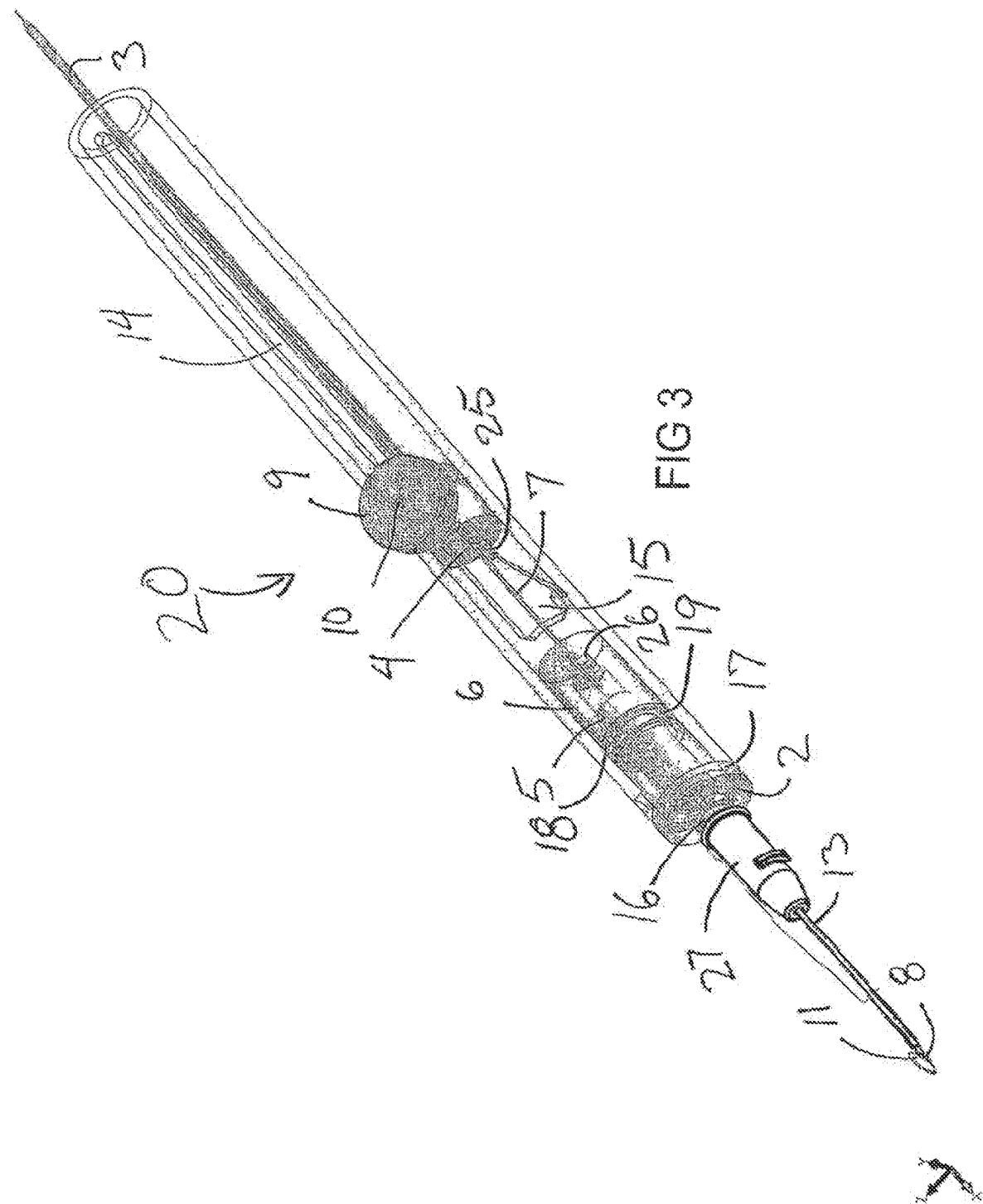
FIG. 3 shows a phantom view of the intravenous catheter insertion device with the safety guidewire advanced.

FIG. 1 shows an exploded view of one embodiment of an intravenous catheter insertion device 20 according to the present invention. FIG. 2 shows an assembly drawing of the intravenous catheter insertion device 20 in an undeployed state, ready for use. FIG. 3 shows a phantom view of the intravenous catheter insertion device 20 with the safety guidewire advanced.

The intravenous catheter insertion device 20 includes an outer housing 1. In the example shown, the outer housing 1 is in the form of an elongated hollow cylinder. Other shapes, including an ergonomic handle shape, are possible. The outer housing 1 may be formed from any material suited for use in medical applications. In one embodiment, the outer housing 1 is preferably molded from a rigid, transparent medical grade plastic. Alternatively, the outer housing 1 may be machined from an extruded plastic tube. There is an elongated slot 14 in the outer housing 1 approximately parallel with the axis of the outer housing 1. The slot 14 is sized to accommodate the dowel pin 10 or provide a connection point to the slider 4 to move the slider along the interior of the outer housing 1. The distal end of the slot 14 widens into a triangular cutout 15, as seen in FIGS. 2 and 3. Other shapes of the cut out 15 are possible.

A front plug 2 is sized to fit onto the distal end of the outer housing 1. The front plug 2 is preferably molded, or alternatively machined, from a rigid, transparent medical grade plastic. The front plug 2 is glued, pinned, welded or otherwise fastened to the distal end of the outer housing 1. The distal end of the front plug 2 includes a luer slip fitting 16 or the like. There is a shoulder or flange 17 to mate with the distal end of the outer housing 1. The proximal end of the front plug 2 has an interlocking member 18 that interlocks with a mating interlocking member 19 on the needle carrier 6. In the example shown, the interlocking member 18 is a tab that interlocks with a corresponding spiral pawl or quarter-turn thread interlocking member 19 on the needle carrier 6. Other geometries for the interlocking members 18, 19 are possible.

In the exemplary embodiment of FIGS. 1-3, the geometry of the slot 14 and the triangular cutout 15 are chosen to operate cooperatively with the rotating interlocking members 18, 19. The slot 14 allows the actuator handle 9 to move in a longitudinal direction with respect to the outer housing 1 to advance the safety guidewire 11 distally, while at the same time restricting lateral motion to avoid premature withdrawal of the access needle 8 and the safety guidewire 11. The widening of the slot 14 at the distal end into a triangular cutout 15 allows the actuator handle 9 to be selectively rotated laterally to disengage the rotating interlocking members 18, 19 and release the biasing member 12 to withdrawal of the access needle 8 and the safety guidewire 11 after the safety guidewire 11 has been fully advanced. If a different geometry or different release mechanism is used in place of the rotating interlocking members 18, 19, the geometry of the slot 14 and the triangular cutout 15 may have to be modified to accommodate the release mechanism.

The needle carrier 6 is shaped and sized to fit inside the outer housing 1. In the embodiment shown in FIGS. 1-3, the needle carrier 6 has a cylindrical shape that is sized to have a sliding fit within the cylindrical outer housing 1. Other shapes are possible and generally the needle carrier 6 will be shaped to be compatible with the interior geometry of the outer housing 1. The needle carrier 6 is preferably molded, or alternatively machined, from any material suited for use in a medical environment. In one embodiment, the needle carrier 6 is formed from a rigid, transparent medical grade plastic. A tubular access needle 8 with a sharpened beveled distal end is attached to a needle carrier nose 5, which is in turn attached to the needle carrier 6. The access needle 8 is preferably made from stainless steel hypodermic tubing. A small cavity or blood flashback chamber that communicates with the lumen of the access needle 8 is positioned within the needle carrier 6, between the needle carrier nose 5 and the needle carrier 6. As mentioned above, the distal end of the needle carrier 6 has an interlocking member 19 that is configured to interlock with a mating interlocking member 18 on the proximal end of the front plug 2. In one exemplary embodiment, the interlocking members 18, 19 are adapted to lock and unlock by rotation of the needle carrier 6 with respect to the front plug 2. The interlocking members 18, 19 may also lock and unlock using a bayonet-type fitting. In the example shown, the interlocking member is a spiral pawl interlocking member 19 that interlocks with a corresponding tab interlocking member 18 on the front plug 2. In one embodiment, the interlocking members lock and/or unlock using less than one revolution of the needle carrier 6. In another embodiment, the interlocking members lock and/or unlock using less than one half a revolution of the needle carrier 6. In still another alternative embodiment, the interlocking members lock and/or unlock using less than one quarter revolution of the needle carrier 6. Other geometries for the interlocking members are possible.

A biasing member 12 is configured to fit between the needle carrier 6 and the front plug 2 to urge them apart. The force of the biasing member 12 is resisted by the interlocking members 18, 19 when the needle carrier 6 and the front plug 2 are locked together. In one embodiment, the biasing member 12 is a spring. Note that in FIG. 1 the biasing member or compression spring 12 is shown in a compressed condition as it would be in the assembled intravenous catheter insertion device 20 in an undeployed condition.

In an alternate embodiment, the interlocking members 18, 19 may be replaced by two members that are bonded together with a breakable bond or a single member with a breakable link. The member or members would be configured to constrain the biasing member 12 until it is desired to withdraw the access needle 8 and safety guidewire 11, at which time, the actuator would break the bond or link to release the biasing member 12. This configuration would make the device 20 more resistant to remanufacturing or reuse.

A tubular intravenous catheter 13, such as an ANGIO-CATH, fits coaxially around the access needle 8. Preferably, the intravenous catheter 13 has a close fit with the access needle 8 and a tapered distal end to minimize any step between the access needle 8 and the intravenous catheter 13 as they are inserted through the wall of a vein. There is a luer fitting 27 or the like on the proximal end of the intravenous catheter 13 that fits onto the luer slip fitting 16 on the distal end of the front plug 2 with a slight interference fit to hold the intravenous catheter 13 in place. Alternative configurations of the device may use a luer lock or other locking mechanism to attach the intravenous catheter 13 to the front plug 2.

A slider 4 is generally cylindrical in shape and sized for a sliding fit inside the cylindrical outer housing 1. Other shapes for the slider 4 are possible depending on the interior geometry of the outer housing 1. The slider 4 is preferably molded, or alternatively machined, from any suitable medical grade material. For example, the slider may be formed from a rigid medical grade plastic. A handle 9 or actuating member attaches to the slider 4 with a dowel pin 10 or other attachment member that extends through the slot 14 in the outer housing 1. The slider 4 fits into the outer housing 1 proximal to the needle carrier 6. A pin 25 extends from the distal surface of the slider 4 and is configured to reversibly engage with a hole, step, boss or similar mating feature 26 on the proximal end of the needle carrier 6. When pin 25 is coupled to the mating feature 26 during the appropriate step of the intravenous catheter insertion and placement procedure, rotation of the slider 4 is transferred to the needle carrier 6 to facilitate engagement and or disengagement of the interlocking members 18, 19. Pin 25 and feature 26 are merely illustrative. Pin 25 may be replaced with a female feature while a mating male feature may be placed on the proximal face of the needle carrier 6. Additionally, the mating features 25, 26 are aligned relative to the elongated slot and the sliding movement of the slider 4 so that distal movement of the slider 4 will engage the mating features 25, 26. Optionally, the device 20 may be configured so that the connection between the slider 4 and needle carrier 6 happens irreversibly when the device 20 is actuated.

As best seen in FIG. 3, a safety guidewire 11 is attached, directly or indirectly, to the slider 4 so that it can be advanced and retracted with the handle 9 attached to the slider 4. In a preferred embodiment, the safety guidewire 11 is constructed of superelastic Nickel-Titanium alloy (Nitinol) wire. Because this type of wire is extremely flexible, it is advantageous to have the safety guidewire 11 enclosed along most of its length to avoid bowing or buckling while advancing the safety guidewire 11. For this reason, the example shown includes a support tubing 7 that is attached to the proximal end of the needle carrier 6. The safety guidewire 11 extends through the internal lumen of a sheath tubing 3 and the proximal end of the safety guidewire 11 is attached at the proximal end of the sheath tubing 3. The distal end of the sheath tubing 3 is in turn attached to the slider 4, indirectly attaching the safety guidewire 11 to the slider 4. The support tubing 7 has a sliding fit inside the sheath tubing 3 so that the two parts telescope together as the slider 4 is advanced in the distal direction. The telescoping action of the support tubing 7 and the sheath tubing 3 provides a variable length support for the proximal portion of the safety guidewire 11 to prevent bowing or buckling of the safety guidewire 11 as it is advanced. The support tubing 7 and the sheath tubing 3 are preferably made from stainless steel hypodermic tubing, however any suitable medical grade plastic material may also be used. In other embodiments, such as those using a larger diameter or stiffer guidewire, the telescoping support tubes may not be necessary, and the proximal end of the safety guidewire 11 may be attached directly to the slider 4.

Figure 4:
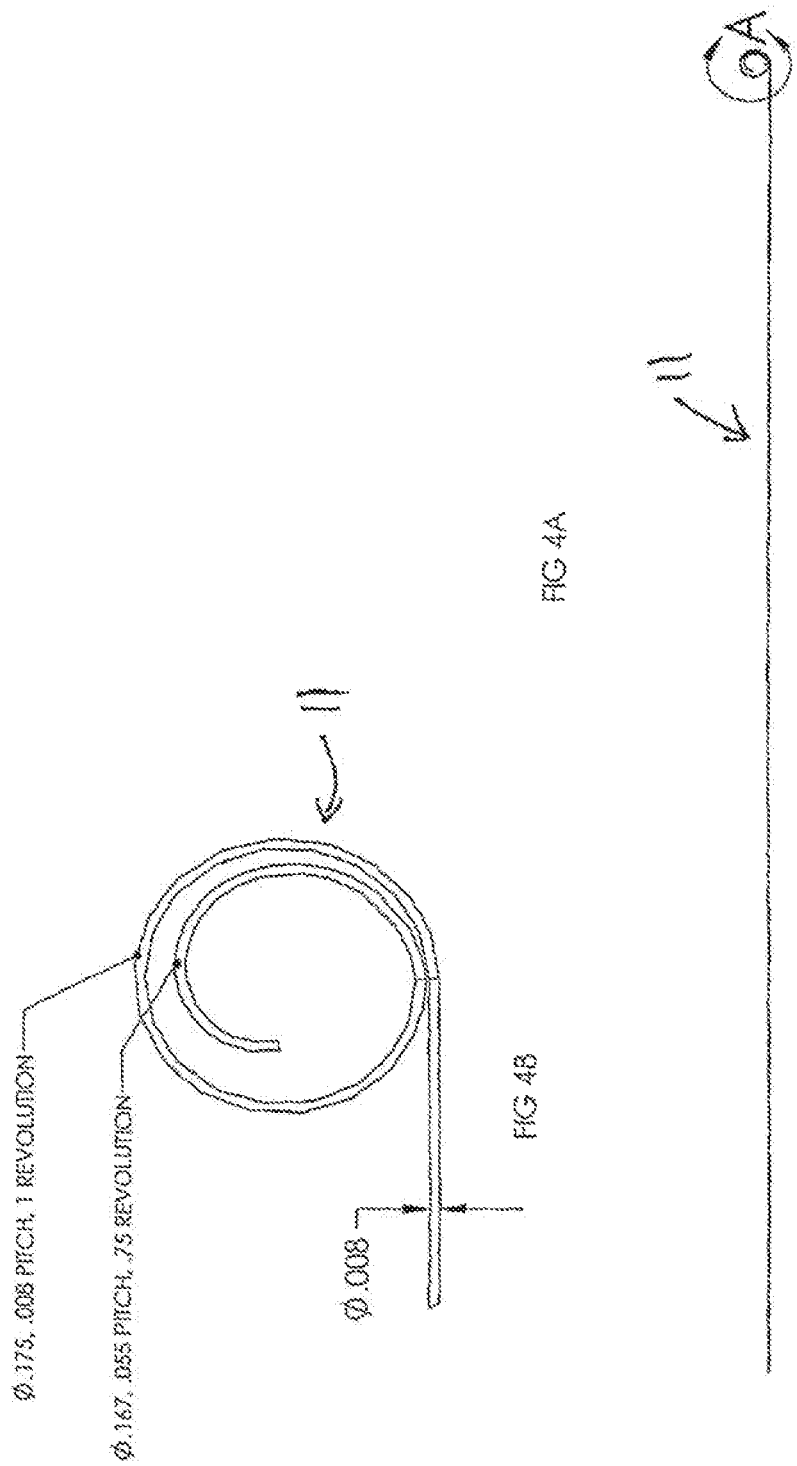
FIGS. 4A and 4B are detail drawings of a safety guidewire for use with the intravenous catheter insertion device.

FIGS. 4A and 4B are detail drawings of a safety guidewire 11 for use with the intravenous catheter insertion device 20. The safety guidewire 11 is preferably constructed of superelastic Nickel-Titanium alloy wire approximately 0.004-0.012 inches in diameter and most preferably approximately 0.008 inches in diameter. As shown in FIG. 4B, the distal end of the safety guidewire 11 is preformed into a tightly wound spiral with an outer diameter smaller than the internal diameter of the target vessel into which it will be inserted. The spiral tip acts as a safety bumper on the guidewire to avoid puncturing or damaging the inside of target vessels. The coiled guidewire tip is particularly useful in protecting fragile or delicate veins. Due to the extreme flexibility of the Nickel-Titanium alloy wire, the spiral distal curve can straighten out when the safety guidewire 11 is withdrawn into the access needle 8 and completely recover into the spiral configuration without plastic deformation when the safety guidewire 11 is advanced out of the access needle 8. In the example shown, the distal end of the safety guidewire 11 has a first, small diameter coil of approximately 0.167 inches in diameter for approximately 0.75 revolutions and a second, larger diameter coil of approximately 0.175 inches in diameter for approximately 1 revolution. The first and second coils are preferably approximately coplanar with one another and preferably approximately coplanar with the straight proximal portion of the guidewire 11 also. Other configurations of the safety guidewire 11 may include: multi-planar, single coil, full radius on the end, and/or a balled end with diameter less than the diameter of the needle.

Figure 5:
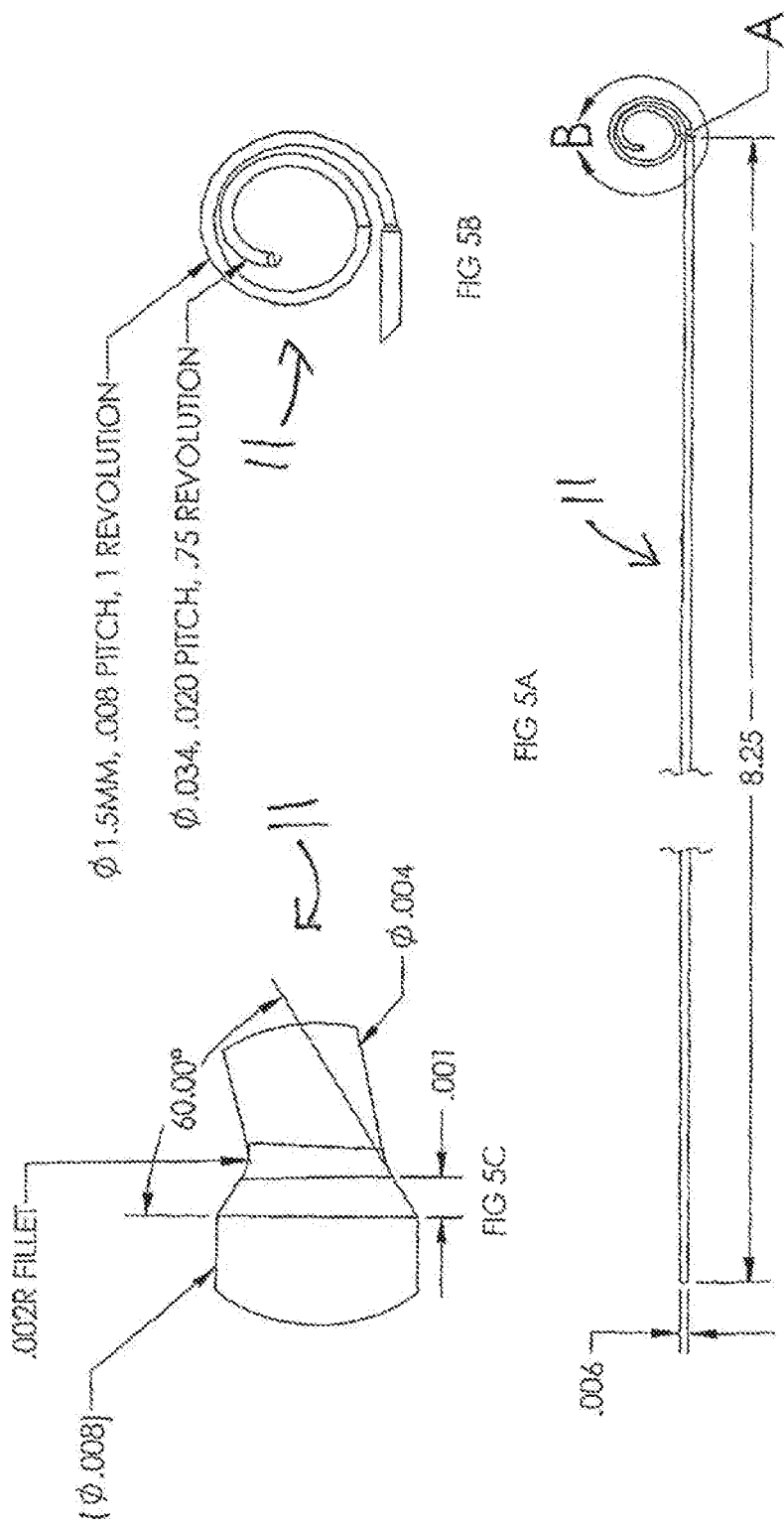
FIGS. 5A, 5B and 5C are detail drawings of another safety guidewire for use with the intravenous catheter insertion device.

FIGS. 5A, 5B and 5C are detail drawings of another safety guidewire 11 for use with the intravenous catheter insertion device 20. In this embodiment, a distal portion of an approximately 0.008 inch diameter Nickel-Titanium alloy wire has been tapered by grinding, stretching, etc., to a diameter of approximately 0.004 inches to make it more flexible and to allow it to be formed into a smaller diameter spiral for use in smaller diameter veins. The spiral curve of the guidewire tip will preferably have an outer diameter smaller than the inner diameter of the target vessel. In the example shown, the spiral curve has a first, small diameter coil of approximately 0.034 inches in diameter for approximately 0.75 revolutions and a second, larger diameter coil of approximately 0.059 inches in diameter for approximately 1 revolution. The first and second coils are preferably approximately coplanar with one another and preferably approximately coplanar with the straight proximal portion of the guidewire 11 also.

Other sizes and geometries of safety guidewire 11 are also possible.

To assemble the intravenous catheter insertion device 20 shown in FIGS. 1-3, the access needle 8 is bonded flush with the proximal face of the needle carrier nose 5, which is in turn bonded into the needle carrier 6. The support tubing 3 is placed into the distal hole in the needle carrier 6, and bonded flush with the proximal face of the blood flashback chamber. The formed safety guidewire 11 is advanced through the lumen of the access needle 8 and support tubing 7 until the coiled section of the safety guidewire 11 meets the access needle 8 bevel. The sheath tubing 3 is slid through the slider 4, and bonded when flush with the distal face. The assembly of the sheath tubing 3 and slider 4 are advanced over the safety guidewire 11. When the safety guidewire 11 is flush with the proximal end of the sheath tubing 3, the two are bonded. The spring 12 is compressed on the needle carrier nose 5, advanced into the front plug 2 and the interlocking members 18, 19 of the front plug 2 and needle carrier 6 are engaged. This assembly of components is placed into the outer housing 1 and advanced until the front plug 2 is flush with the outer housing 1, and then the front plug 2 is rotated for proper alignment. The front plug 2 is then bonded to the outer housing 1. The dowel pin 10 and handle 9 are pressed together with the slider 4. The handle 9 is slid proximally to withdraw the safety guidewire 11 into the access needle 8, thereby straightening out the spiral distal curve. An intravenous catheter 13 is then mounted coaxially around the access needle 8. Optionally, the intravenous catheter 13 insertion device may be provided with a needle cover or other protective packaging. The assembled intravenous catheter insertion device 20, including the intravenous catheter 13, is then packaged, labeled and sterilized.

The preceding assembly description is provided to illustrate one example of a process for manufacturing an embodiment of the intravenous catheter insertion device 20 and also so that the interrelationship of the various components will be understood. Modifications and variations of this description are expected depending upon specific selected assembly or manufacturing techniques. For example, components that are bonded may be redesigned to be formed from a single integrated piece and the like. The manufacturing process can be modified and adapted for assembling other embodiments of the intravenous catheter insertion device 20.

Figure 6:
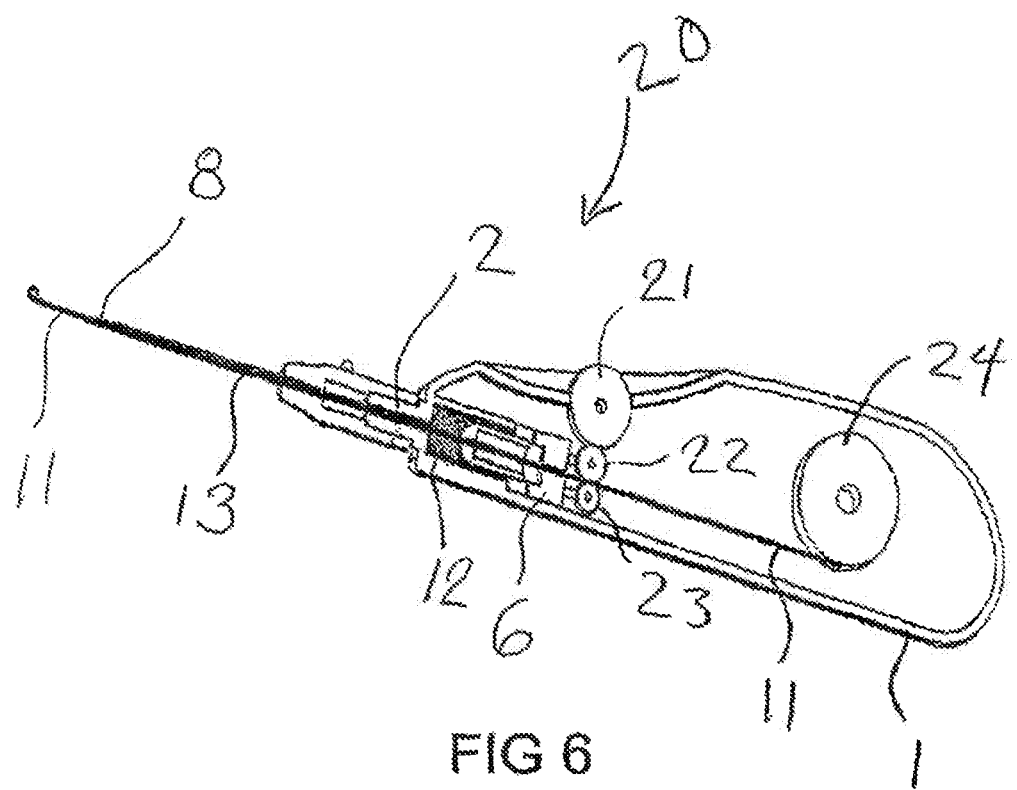
FIG. 6 shows another embodiment of an intravenous catheter insertion device according to the present invention.

FIG. 6 shows an interior view of another embodiment of an intravenous catheter insertion device 20 according to the present invention. This embodiment is similar in many respects to the intravenous catheter insertion device 20 of FIGS. 1-3. The intravenous catheter insertion device 20 includes an outer housing 1, front plug 2, which may optionally be molded integrally with the outer housing 1, a needle 8 attached to a needle carrier 6, a safety guidewire 11, spring 12 and intravenous catheter 13. However, the functions of the handle 9 and the slider 4 have been replaced by a thumbwheel 21 that engages a pair of friction wheels 22, 23, which are in contact with the safety guidewire 11. Likewise, the functions of the sheath tubing 3 and the support tubing 7 have been replaced by a guidewire spool 24. These features allow the intravenous catheter insertion device 20 to be constructed in a more compact configuration. In use, the safety guidewire 11 is advanced by turning the thumbwheel 21. A lateral movement of the thumbwheel 21 disengages the needle carrier 6 from the front plug 2, allowing the biasing member 12 to expand, thereby retracting the needle 8 and the safety guidewire 11 into the outer housing 1. Alternatively, a separate button, lever or other actuation member can be provided to actuate the withdrawal of the needle 8 and the safety guidewire 11. The guidewire spool 24 may optionally include a rotary spring or similar mechanism (not shown) to assist in the retraction of the safety guidewire 11 into the outer housing 1.

FIGS. 7-9 illustrate a method of inserting an intravenous catheter using an intravenous catheter insertion device 20, such as those described in FIGS. 1-3 or FIG. 6. The intravenous catheter insertion device 20 is a single-use, non-reusable device supplied to the physician or medical practitioner sterile in a ready-to-use, undeployed condition as shown in FIG. 2. In use, the physician uses the outer housing 1 as a handle to manipulate the intravenous catheter insertion device 20. With the device in the undeployed condition, the access needle 8 is used to puncture a vein, as shown in FIG. 7. When venous blood is observed in the blood flashback chamber, the distal tip of the access needle 8 is the lumen of the vein. The physician can then advance the handle 9 in the distal direction to extend the safety guidewire 11 out of the access needle 8 into the lumen of the vein. The distal portion of the safety guidewire 11 assumes its spiral configuration to act as a safety bumper to prevent accidental puncture of the far wall of the vein or other damage to the vein. With the safety guidewire 11 thus deployed, the physician can safely continue advancing the intravenous catheter insertion device 20 until the distal tip of the intravenous catheter 13 is in the lumen of the vein. Once the intravenous catheter 13 is inserted far enough into the vein, the physician rotates the handle 9 that rotates the slider 4, which in turn rotates the needle carrier 6 and disengages the interlocking member 18 of the needle carrier 6 from the mating interlocking member 19 on the front plug 2. (In the exemplary embodiment described above, the handle moves in a counterclockwise direction as allowed by the triangular cutout 15 at the distal end of the slot 14 in the outer housing 1. Additional structural features of the actuator mechanism are shown in more detail in FIGS. 1-3.) When the handle 9 is released, the biasing element (here a compression spring 12) urges the needle carrier 6 and the slider 4 in the proximal direction, thus simultaneously withdrawing the access needle 8 and the safety guidewire 11 into the outer housing 1, leaving only the intravenous catheter 13 in the lumen of the vein. FIG. 8 shows the access needle 8 and the safety guidewire 11 withdrawing into the outer housing 1. The shape of the triangular cutout 15 allows the handle 9 to make a smooth transition into the elongated slot 14 as it moves proximally under the influence of the biasing element 12. Finally, the intravenous catheter 13 is disengaged from the luer slip 16 fitting on the distal end of the front plug 2, as shown in FIG. 9, and a source of intravenous fluid, a syringe or other device is attached to the luer fitting 27 of the intravenous catheter 13.

While it is desirable for the intravenous catheter insertion device 20 to withdraw the access needle 8 and the safety guidewire 11 simultaneously, the actuator mechanism could also be modified to withdraw the access needle 8 and the safety guidewire 11 sequentially. For example, the actuator mechanism could withdraw the access needle 8 first and then, after a slight delay, withdraw the safety guidewire 11.

Alternatively, the actuator mechanism could be modified to require two separate motions of one actuator member or selective movements of two separate actuator members to withdraw the access needle 8 and the safety guidewire 11 selectively.

In an alternative embodiment of the intravenous catheter insertion device 20, the compression spring 12 may be omitted from the actuator mechanism, thus allowing the access needle 8 and the safety guidewire 11 to be withdrawn manually using the handle 9. Once the intravenous catheter 13 has been inserted into the patient's vein, the handle 9 is rotated laterally to disengage the needle carrier 6 from the front plug 2, then the handle 9 is moved proximally along the slot 14 to withdraw the access needle 8 and the safety guidewire 11 into the outer housing 1.

While the present invention has been described herein with respect to the exemplary embodiments and the best mode for practicing the invention, it will be apparent to one of ordinary skill in the art that many modifications, improvements and subcombinations of the various embodiments, adaptations and variations can be made to the invention without departing from the spirit and scope thereof. For example, all dimensions and materials included in the specification or drawings are intended only as examples of presently preferred embodiments and are not intended to limit the scope of the invention.

What is claimed is:

1. A method for treating a patient, comprising:
   holding a catheter insertion device comprising:
      a housing;
      a catheter including a catheter hub;
      a needle extending through the catheter, the needle having a distal end extending distal of a distal end of the catheter; and
      a guidewire coupled to a thumbwheel, the thumbwheel rotatably fastened at a front end of the housing, the thumbwheel extending through an opening in the housing, wherein rotation of the thumbwheel advances a distal end of the guidewire through a lumen of the needle;
   inserting the distal end of the needle and the distal end of the catheter into a blood vessel of the patient;
   rotating the thumbwheel to advance the distal end of the guidewire out of the lumen of the needle into the blood vessel without moving the catheter and the needle;
   extending the distal end of the catheter further into the blood vessel by moving the catheter over the guidewire in the blood vessel; and
   removing the needle and the guidewire from the catheter.

2. The method according to claim 1, wherein the catheter insertion device further comprises a blood flashback chamber, further comprising observing blood in the blood flashback chamber after inserting the needle and the catheter into the blood vessel prior to rotating the thumbwheel.

3. The method according to claim 1, wherein an axis of rotation of the thumbwheel is perpendicular to the guidewire.

4. The method according to claim 1, wherein the thumbwheel engages a friction wheel in the housing, and wherein rotating the thumbwheel rotates the friction wheel to advance the guidewire.

5. The method according to claim 1, wherein the needle is attached to a needle carrier having a proximal end disposed in the housing.

6. The method according to claim 5, wherein the catheter insertion device further comprises an actuator mechanism including a biasing member positioned between a distal end of the housing and the needle carrier, and wherein activating the actuator mechanism releases the biasing member.

7. The method according to claim 6, wherein activating the actuator mechanism to release the biasing member simultaneously retracts the distal end of the needle and the distal end of the guidewire into the housing.

8. The method according to claim 6, wherein activating the actuator mechanism comprises moving the thumbwheel laterally to disengage the needle carrier from a front plug in the housing.

9. The method according to claim 1, wherein the guidewire has a proximal portion having a first diameter and a distal portion having a second diameter less than the first diameter, wherein the distal portion is formed into a coiled configuration at the distal end of the guidewire, and wherein advancing the distal end of the guidewire out of the lumen of the needle transitions the distal end of the guidewire from a straight configuration to the coiled configuration.

10. The method according to claim 1, wherein the distal end of the guidewire has a coiled configuration including a first coil in a first coil plane and a second coil in a second coil plane different from the first coil plane, and wherein advancing the distal end of the guidewire out of the lumen of the needle transitions the distal end of the guidewire from a straight configuration to the coiled configuration.

11. The method according to claim 10, wherein advancing the distal end of the guidewire out of the lumen of the needle transitions the distal end of the guidewire to the coiled configuration without plastic deformation of the guidewire.

12. The method according to claim 1, wherein:
   the distal end of the guidewire has a coiled configuration, comprising:
      a first coil extending from a straight portion of the guidewire, the first coil lying substantially in a first coil plane; and
      a second coil extending from the first coil, the second coil lying substantially in a second coil plane parallel to the first coil plane, the second coil having a diameter less than or equal to a diameter of the first coil, wherein a line orthogonal to the first coil plane and the second coil plane is substantially orthogonal to the straight portion of the guidewire, and
   advancing the distal end of the guidewire out of the lumen of the needle transitions the distal end of the guidewire from a straight configuration to the coiled configuration.

13. The method according to claim 12, wherein a distal tip of the guidewire meets a bevel of the needle in a fully withdrawn position, and wherein moving the catheter over the guidewire in the blood vessel comprises moving the distal end of the catheter over the distal end of the guidewire in the coiled configuration.

14. The method according to claim 1, wherein the catheter hub is coupled to a distal end of the housing via an interference fit, wherein moving the catheter over the guidewire in the blood vessel comprises uncoupling the catheter hub from the distal end of the housing.

15. The method according to claim 1, wherein the catheter hub is coupled to a member extending from a distal end of the housing, and wherein moving the catheter over the guidewire in the blood vessel comprises uncoupling the catheter hub from the member.

\* \* \* \* \*